United States Patent
Ray, II

(10) Patent No.: US 9,707,229 B2
(45) Date of Patent: *Jul. 18, 2017

(54) COMPOSITIONS AND METHODS FOR TREATING AN INFECTION

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,172

(22) Filed: Dec. 18, 2015

(65) Prior Publication Data

US 2017/0173003 A1 Jun. 22, 2017

(51) Int. Cl.
| | |
|---|---|
| *A61K 31/496* | (2006.01) |
| *A61K 31/351* | (2006.01) |
| *A61K 45/06* | (2006.01) |
| *A61K 47/26* | (2006.01) |
| *A61K 47/34* | (2017.01) |
| *A61K 9/00* | (2006.01) |
| *A61H 35/00* | (2006.01) |

(52) U.S. Cl.
CPC ......... *A61K 31/496* (2013.01); *A61H 35/006* (2013.01); *A61K 9/0014* (2013.01); *A61K 31/351* (2013.01); *A61K 45/06* (2013.01); *A61K 47/26* (2013.01); *A61K 47/34* (2013.01)

(58) Field of Classification Search
CPC ............... A61K 31/496; A61K 31/351; A61K 2300/00; A61K 45/06; A61K 9/0014; A61K 47/26; A61K 47/34; A61H 35/006
See application file for complete search history.

(56) References Cited

U.S. PATENT DOCUMENTS

| 2009/0016990 A1* | 1/2009 | Alberte | A61K 31/185 |
| | | | 424/85.5 |
| 2014/0256826 A1* | 9/2014 | Lemire | A01N 31/08 |
| | | | 514/703 |

OTHER PUBLICATIONS

PCCA Science, "Technical Report: The Antimicrobial Activity of Itraconazole and LoxaSperse TM Against Biofilms of C. albicans," 2013, www.ccarx.com, pp. 1-2.*
U.S. Appl. No. 14/819,342, filed Aug. 5, 2015, Applicant is CMPD Licensing, LLC, Inventor is Jay Richard Ray, II.
Label for Diflucan (Fluconazole Tablets), Distributed by Roerig, a Division of Pfizer, Mar. 2013 (35 pages).
Label (Package Insert) for Azithromycin, Distributed by SICOR Pharmaceuticals, Inc., Dec. 2016 (18 pages).
Label for Bactroban (mupirocin), Distributed by GlaxoSmithKline, Dec. 2015 (10 pages).
FDA Prescribing Information for Nystatin Powder, Distributed by Mayne Pharma, Summarized by www.drugs.com (5 pages).
PCCA, Brochure for LoxaSperse, "Powder Excipient Base for Use in Nebulization and Irrigation Compounds", 2013 (3 pages).
PCCA, "New, Exclusive PCCA Base, XyliFos™: Boost the LoxaSperse™ Power in Nasal Nebulization and Decrease your Cost", Aug. 7, 2015 (2 pages).

* cited by examiner

*Primary Examiner* — Sreeni Padmanabhan
*Assistant Examiner* — Jody Karol
(74) *Attorney, Agent, or Firm* — Akerman LLP

(57) ABSTRACT

The present application relates to compounded compositions, methods of making compounded compositions, kits comprising compounded compositions, containers comprising compounded compositions, and methods of using compounded compositions. The present application also relates to anti-infective agents and methods of using anti-infective agents. For example, disclosed herein are compounded compositions comprising an anti-bacterial agent, an anti-fungal agent, and an excipient base and methods of using a compounded composition to treat or prevent a bacterial infection, a fungal infection, or both, or a suspected bacterial infection, a suspected fungal infection, or both. This abstract is intended as a scanning tool for purposes of searching in the particular art and is not intended to be limiting of the present invention.

10 Claims, No Drawings

COMPOSITIONS AND METHODS FOR TREATING AN INFECTION

FIELD OF THE INVENTION

The present application relates to compounded compositions, methods of making compounded compositions, and methods of using compounded compositions to treat or prevent an infection. The present application also relates to anti-infective agents and methods of using anti-infective agents to treat or prevent an infection.

BACKGROUND OF THE INVENTION

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Foot infections can be difficult problems for physicians to treat because of the biomechanical complexities of the extremity and the underlying circumstances that cause the infections. Soft tissue infections in the foot consist of any infectious process affecting the skin, subcutaneous tissue, adipose tissue, superficial or deep fascia, ligaments, tendons, tendon sheaths, joints, and/or joint capsules. Considering that there are more than 20 joints, 44 tendons, approximately 100 ligaments, 4 major compartments, and numerous fascial planes in the normal foot, the potential for complex problems is high.

Bacterial infections of the feet can occur as collections of pus, such as an abscess following a puncture wound or an infected hair follicle. These types of infections are usually red and elevated, and sometimes can be mistaken for an insect bite. There are many types of bacteria that cause an abscess, but staph are a leading cause. Bacterial skin infections can also resemble a rash, appearing as a reddened, tender, and warm area of skin. This type of infection is called cellulitis and can spread quickly, leading to red streaks that move from the foot toward the leg. The appearance of streaks is known as lymphangitis, which means the infection is spreading toward the lymph nodes. Cellulitis and lymphangitis can be caused by a variety of types of bacteria, but staph and sometimes *streptococcus* are the most common causes. Any infection, especially cellulitis and lymphangitis, requires prompt medical attention to avoid further spreading and complications. If left untreated, then some infections can spread to deeper tissues, including bone.

Certain fungal infections of the skin known as tinea infections are caused by dermatophytes, which are members of the *Trichophyton, Microsporum*, and *Epidermophyton* species. These mold-like fungi thrive in warm, moist areas, thriving on the dead tissues of hair, nails, and outer skin layers. Tinea infections include tinea pedis, known as athlete's foot; tinea corporis, known as ringworm; tinea capitis, a fungal infection of the scalp that can cause hair loss; tinea cruris, known as jock itch or tinea of the groin; tinea unguum, which is tinea of the nails; and tinea *versicolor*, a superficial fungal infection that produces brown, tan, or white spots on the trunk of the body. Tinea infections are contagious and can be passed through direct contact or by contact with clothing, from shower and pool surfaces, and even from pets.

Athlete's foot or tinea pedis is by far the most common form, with more than 12 million people in the United States suffering from the disease per year. It presents with redness, itching, burning, cracking, scaling, swelling, and occasionally bleeding. Athlete's foot includes toe web infections, moccasin type infections, and vesicular type infections. The condition generally includes small vesicles, fissures, scaling, maceration, hyperkeratinization, and eroded areas between the toes and on the plantar surface of the foot, as well as on other skin areas. For example, the nails may show thickening, pitting, and subungal debris.

Reoccurrences of the infection are frequent. For some subjects, such as those also diagnosed with diabetes or circulatory problems, or obese subjects, tinea infections and their treatment can be quite serious. The source of the affliction often is a public safety and health concern, as the occurrence of tinea pedis is higher in public areas such as locker rooms, public showers, sports facilities, and the like.

Moreover, there are at least 3 different types of nail infections caused by fungi. The most common infection is frequently caused by *Trichophyton rubrum* and affects the nail bed and the area beneath the nail. Another type of infection affects only the nail surface and creates white or light colored patches. This second type of fungal infection is unusual and represents only about 10% of the reported cases. A third type of fungal infection affects the nail root and usually afflicts persons with impaired immune defense. A fourth (and unusual) type is caused by an infection of yeast fungi. Infections by yeast most often only affect nails that already are infected or damaged in some way.

The fungi are invasive to the keratin nail tissue. Apart from becoming discolored and brittle, the nail may often separate from the nail bed. In addition, pain and difficulty in wearing foot apparel is often experienced. Initially, the disease affects only one nail, typically one nail of the foot, and is thereafter spread to more nails. The palms of the hands and the soles of the feet may frequently be affected as well. When the skin is affected, red spots frequently occur and the skin may peel off. Nail fungal infections are one of the hardest forms of external infection to treat, of which infections of toe nails are the most difficult to treat.

Despite advances in the understanding of the pathology of bacterial infections and fungal infections, there is still a need for compositions and methods that efficiently treat or prevent the progression and reoccurrence of bacterial infections and/or fungal infections that affect at least part of one or both feet.

BRIEF SUMMARY OF THE INVENTION

Disclosed herein is a compounded composition for treating an infection.

Disclosed herein can be a compounded composition comprising an anti-bacterial agent, an anti-fungal agent, and an excipient base powder comprising a blend of micronized xylitol and poloxamers.

Disclosed herein is a compounded composition comprising mupirocin, an anti-fungal agent, and an excipient base powder comprising a blend of micronized xylitol and poloxamers.

Disclosed herein is a compounded composition comprising an anti-bacterial agent, itraconazole, and an excipient base powder comprising a blend of micronized xylitol and poloxamers.

Disclosed herein is a compounded composition comprising mupirocin, itraconazole, and an excipient base powder comprising a blend of micronized xylitol and poloxamers.

Disclosed herein is a compounded composition comprising mupirocin, itraconazole, an excipient base powder comprising a blend of micronized xylitol and poloxamers, and at least one additional anti-infective agent.

Disclosed herein is a compounded composition comprising azithromycin, an anti-fungal agent, and an excipient base powder comprising a blend of micronized xylitol and poloxamers.

Disclosed herein is a compounded composition comprising an anti-bacterial agent, fluconazole, and an excipient base powder comprising a blend of micronized xylitol and poloxamers.

Disclosed herein is a compounded composition comprising azithromycin, fluconazole, and an excipient base powder comprising a blend of micronized xylitol and poloxamers.

Disclosed herein is a compounded composition comprising azithromycin, fluconazole, an excipient base powder comprising a blend of micronized xylitol and poloxamers, and at least one additional anti-infective agent.

Disclosed herein can be a compounded composition comprising mupirocin, nystatin, and an excipient base powder comprising a blend of micronized xylitol and poloxamers.

Disclosed herein is a capsule comprising a disclosed compounded composition.

Disclosed herein is a capsule comprising a compounded composition, wherein the compounded composition comprises an anti-bacterial agent and an anti-fungal agent.

Disclosed herein is a capsule comprising a compounded composition, wherein the compounded composition comprises an anti-bacterial agent, an anti-fungal agent, and Loxasperse™ excipient base powder.

Disclosed herein is a capsule comprising a compounded composition, wherein the compounded composition comprises an anti-bacterial agent, an anti-fungal agent, and an excipient base powder comprising a blend of micronized xylitol and poloxamers.

Disclosed herein is a capsule comprising a compounded composition, wherein the compounded composition comprises mupirocin and itraconazole.

Disclosed herein is a capsule comprising a compounded composition comprising mupirocin, an anti-fungal agent, and an excipient base powder comprising a blend of micronized xylitol and poloxamers.

Disclosed herein is a capsule comprising a compounded composition comprising an anti-bacterial agent, itraconazole, and an excipient base powder comprising a blend of micronized xylitol and poloxamers.

Disclosed herein is a capsule comprising a compounded composition comprising mupirocin, itraconazole, and an excipient base powder comprising a blend of micronized xylitol and poloxamers.

Disclosed herein is a capsule comprising a compounded composition comprising mupirocin, itraconazole, an excipient base powder comprising a blend of micronized xylitol and poloxamers, and at least one additional anti-infective agent.

Disclosed herein is a capsule comprising a compounded composition comprising mupirocin, itraconazole, and Loxasperse™ excipient base powder.

Disclosed herein is a capsule comprising a compounded composition, wherein the compounded composition comprises azithromycin and fluconazole.

Disclosed herein is a capsule comprising a compounded composition comprising azithromycin, an anti-fungal agent, and an excipient base powder comprising a blend of micronized xylitol and poloxamers.

Disclosed herein is a capsule comprising a compounded composition comprising an anti-bacterial agent, fluconazole, and an excipient base powder comprising a blend of micronized xylitol and poloxamers.

Disclosed herein is a capsule comprising a compounded composition comprising azithromycin, fluconazole, and an excipient base powder comprising a blend of micronized xylitol and poloxamers.

Disclosed herein is a capsule comprising a compounded composition comprising azithromycin, fluconazole, an excipient base powder comprising a blend of micronized xylitol and poloxamers, and at least one additional anti-infective agent.

Disclosed herein is a capsule comprising a compounded composition comprising azithromycin, fluconazole, and Loxasperse™ excipient base powder.

Disclosed herein is a capsule comprising a compounded composition, wherein the compounded composition comprises mupirocin and nystatin.

Disclosed herein is a capsule comprising a compounded composition comprising mupirocin, an anti-fungal agent, and an excipient base powder comprising a blend of micronized xylitol and poloxamers.

Disclosed herein is a capsule comprising a compounded composition comprising an anti-bacterial agent, nystatin, and an excipient base powder comprising a blend of micronized xylitol and poloxamers.

Disclosed herein is a capsule comprising a compounded composition comprising mupirocin, nystatin, and an excipient base powder comprising a blend of micronized xylitol and poloxamers.

Disclosed herein is a capsule comprising a compounded composition comprising mupirocin, nystatin, an excipient base powder comprising a blend of micronized xylitol and poloxamers, and at least one additional anti-infective agent.

Disclosed herein is a capsule comprising a compounded composition comprising mupirocin, nystatin, and Loxasperse™ excipient base powder.

Disclosed herein is a capsule comprising an anti-bacterial agent. Disclosed herein is a capsule comprising mupirocin. Disclosed herein is a capsule comprising azithromycin. Disclosed herein is a capsule comprising an anti-fungal agent. Disclosed herein is a capsule comprising itraconazole. Disclosed herein is a capsule comprising fluconazole. Disclosed herein is a capsule comprising nystatin.

Disclosed herein is a container comprising a disclosed compounded composition.

Disclosed herein is a container comprising a compounded composition, wherein the compounded composition can comprise an anti-bacterial agent, an anti-fungal agent, and an excipient base powder comprising a blend of micronized xylitol and poloxamers.

Disclosed herein is a container comprising one or more capsules, each capsule comprising a compounded composition, wherein the compounded composition can comprise an anti-bacterial agent, an anti-fungal agent, and an excipient base powder comprising a blend of micronized xylitol and poloxamers.

Disclosed herein is a container comprising a compounded composition, wherein the compounded composition can comprise mupirocin, itraconazole, and an excipient base powder comprising a blend of micronized xylitol and poloxamers.

Disclosed herein is a container comprising one or more capsules, each capsule comprising a compounded composition, wherein the compounded composition can comprise mupirocin, itraconazole, and an excipient base powder comprising a blend of micronized xylitol and poloxamers.

Disclosed herein is a container comprising a compounded composition, wherein the compounded composition can comprise an anti-bacterial agent, itraconazole, and an excipient base powder comprising a blend of micronized xylitol and poloxamers.

Disclosed herein is a container comprising a compounded composition, wherein the compounded composition can comprise mupirocin, an anti-fungal agent, and an excipient base powder comprising a blend of micronized xylitol and poloxamers.

Disclosed herein is a container comprising a compounded composition, wherein the compounded composition can comprise mupirocin, itraconazole, an excipient base powder comprising a blend of micronized xylitol and poloxamers, and at least one additional anti-infective agent.

Disclosed herein is a container comprising a compounded composition, wherein the compounded composition can comprise azithromycin, fluconazole, and an excipient base powder comprising a blend of micronized xylitol and poloxamers.

Disclosed herein is a container comprising one or more capsules, each capsule comprising a compounded composition, wherein the compounded composition can comprise azithromycin, fluconazole, and an excipient base powder comprising a blend of micronized xylitol and poloxamers.

Disclosed herein is a container comprising a compounded composition, wherein the compounded composition can comprise an anti-bacterial agent, fluconazole, and an excipient base powder comprising a blend of micronized xylitol and poloxamers.

Disclosed herein is a container comprising a compounded composition, wherein the compounded composition can comprise azithromycin, an anti-fungal agent, and an excipient base powder comprising a blend of micronized xylitol and poloxamers.

Disclosed herein is a container comprising a compounded composition, wherein the compounded composition can comprise azithromycin, fluconazole, an excipient base powder comprising a blend of micronized xylitol and poloxamers, and at least one additional anti-infective agent.

Disclosed herein is a container comprising a compounded composition, wherein the compounded composition can comprise mupirocin, nystatin, and an excipient base powder comprising a blend of micronized xylitol and poloxamers.

Disclosed herein is a container comprising one or more capsules, each capsule comprising a compounded composition, wherein the compounded composition can comprise mupirocin, nystatin, and an excipient base powder comprising a blend of micronized xylitol and poloxamers.

Disclosed herein is a container comprising a compounded composition, wherein the compounded composition can comprise an anti-bacterial agent, nystatin, and an excipient base powder comprising a blend of micronized xylitol and poloxamers.

Disclosed herein is a container comprising a compounded composition, wherein the compounded composition can comprise mupirocin, an anti-fungal agent, and an excipient base powder comprising a blend of micronized xylitol and poloxamers.

Disclosed herein is a container comprising a compounded composition, wherein the compounded composition can comprise mupirocin, nystatin, an excipient base powder comprising a blend of micronized xylitol and poloxamers, and at least one additional anti-infective agent.

Disclosed herein is a container comprising an anti-bacterial agent. Disclosed herein is a container comprising an anti-fungal agent.

Disclosed herein is a kit comprising a disclosed composition.

Disclosed herein is a kit, comprising: one or more containers, each comprising a compounded composition, wherein the compounded composition can comprise a therapeutically effective amount of an anti-bacterial agent, a therapeutically effective amount of an anti-fungal agent, and an amount of an excipient base powder comprising a blend of micronized xylitol and poloxamers.

Disclosed herein is a kit, comprising: one or more containers, each comprising a compounded composition, wherein the compounded composition can comprise a therapeutically effective amount of an anti-bacterial agent, a therapeutically effective amount of an anti-fungal agent, and an excipient base powder comprising a blend of micronized xylitol and poloxamers, and instructions for using the compounded composition.

Disclosed herein is a kit, comprising: one or more containers, each comprising a compounded composition, wherein the compounded composition can comprise a therapeutically effective amount of an anti-bacterial agent, a therapeutically effective amount of an anti-fungal agent, and an excipient base powder comprising a blend of micronized xylitol and poloxamers, a foot bath, and instructions for using the compounded composition.

Disclosed herein is a kit, comprising: one or more containers, each comprising a compounded composition, wherein the compounded composition can comprise a therapeutically effective amount of mupirocin, a therapeutically effective amount of itraconazole, and an excipient base powder comprising a blend of micronized xylitol and poloxamers.

Disclosed herein is a kit, comprising: one or more containers, each comprising a compounded composition, wherein the compounded composition can comprise a therapeutically effective amount of mupirocin, a therapeutically effective amount of itraconazole, and an excipient base powder comprising a blend of micronized xylitol and poloxamers, and instructions for using the compounded composition.

Disclosed herein is a kit, comprising: one or more containers, each comprising a compounded composition, wherein the compounded composition can comprise a therapeutically effective amount of mupirocin, a therapeutically effective amount of itraconazole, and an excipient base powder comprising a blend of micronized xylitol and poloxamers, a foot bath, and instructions for using the compounded composition.

Disclosed herein is a kit, comprising: one or more containers, each comprising a compounded composition, wherein the compounded composition can comprise a therapeutically effective amount of azithromycin, a therapeutically effective amount of fluconazole, and an excipient base powder comprising a blend of micronized xylitol and poloxamers.

Disclosed herein is a kit, comprising: one or more containers, each comprising a compounded composition, wherein the compounded composition can comprise a therapeutically effective amount of azithromycin, a therapeutically effective amount of fluconazole, and an excipient base powder comprising a blend of micronized xylitol and poloxamers, and instructions for using the compounded composition.

Disclosed herein is a kit, comprising: one or more containers, each comprising a compounded composition, wherein the compounded composition can comprise a therapeutically effective amount of azithromycin, a therapeutically effective amount of fluconazole, and an excipient base powder comprising a blend of micronized xylitol and poloxamers, a foot bath, and instructions for using the compounded composition.

Disclosed herein is a kit comprising an anti-bacterial agent and an anti-fungal agent.

Disclosed herein is a kit, comprising: one or more containers comprising a therapeutically effective amount of an anti-bacterial agent and one or more containers comprising a therapeutically effective amount of an anti-fungal agent.

Disclosed herein is a kit, comprising: one or more containers comprising a therapeutically effective amount of an anti-bacterial agent or one or more containers comprising a therapeutically effective amount of an anti-fungal agent, a foot bath, and instructions for using the anti-bacterial agent and the anti-fungal agent.

Disclosed herein is a kit, comprising: one or more containers comprising a therapeutically effective amount of an anti-bacterial agent or one or more containers comprising a therapeutically effective amount of an anti-fungal agent, a foot bath, and instructions for using the anti-bacterial agent and the anti-fungal agent.

Disclosed herein is a kit, comprising: one or more containers comprising a therapeutically effective amount of mupirocin and one or more containers comprising a therapeutically effective amount of itraconazole.

Disclosed herein is a kit, comprising: one or more containers comprising a therapeutically effective amount of mupirocin and one or more containers comprising a therapeutically effective amount of itraconazole, and instructions for using the mupirocin and the itraconazole.

Disclosed herein is a kit, comprising: one or more containers comprising a therapeutically effective amount of mupirocin, one or more containers comprising a therapeutically effective amount of itraconazole, a foot bath, and instructions for using the mupirocin and the itraconazole.

Disclosed herein is a kit, comprising: one or more containers comprising a therapeutically effective amount of mupirocin, one or more containers comprising a therapeutically effective amount of itraconazole, a foot bath, one or more scoops, one or more mixing containers, a diluent, and instructions for using the mupirocin and the itraconazole.

Disclosed herein is a kit, comprising: one or more containers comprising a therapeutically effective amount of azithromycin and one or more containers comprising a therapeutically effective amount of fluconazole.

Disclosed herein is a kit, comprising: one or more containers comprising a therapeutically effective amount of azithromycin, one or more containers comprising a therapeutically effective amount of fluconazole, and instructions for using the mupirocin and the itraconazole.

Disclosed herein is a kit, comprising: one or more containers comprising a therapeutically effective amount of azithromycin, one or more containers comprising a therapeutically effective amount of fluconazole, a foot bath, and instructions for using the mupirocin and the itraconazole.

Disclosed herein is a kit, comprising: one or more containers, each comprising a therapeutically effective amount of azithromycin, one or more containers comprising a therapeutically effective amount of fluconazole, a foot bath, one or more scoops, one or more mixing containers, a diluent, and instructions for using the azithromycin and the fluconazole.

Disclosed herein is a kit, comprising: one or more containers comprising a therapeutically effective amount of mupirocin and one or more containers comprising a therapeutically effective amount of nystatin.

Disclosed herein is a kit, comprising: one or more containers comprising a therapeutically effective amount of mupirocin, one or more containers comprising a therapeutically effective amount of nystatin, and instructions for using the mupirocin and the nystatin.

Disclosed herein is a kit, comprising: one or more containers comprising a therapeutically effective amount of mupirocin, one or more containers comprising a therapeutically effective amount of nystatin, a foot bath, and instructions for using the mupirocin and the nystatin.

Disclosed herein is a kit, comprising: one or more containers comprising a therapeutically effective amount of mupirocin, one or more containers comprising a therapeutically effective amount of nystatin, a foot bath, one or more scoops, a mixing container, one or more keys, a diluent, and instructions for using the mupirocin, and the nystatin.

Disclosed herein is a method of making a compounded composition comprising an anti-bacterial agent and an anti-fungal agent.

Disclosed herein is a method of making a compounded composition, the method comprising: mixing a therapeutically effective amount of an anti-bacterial agent and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of mupirocin and a therapeutically effective amount of itraconazole with an excipient base powder comprising a blend of micronized xylitol and poloxamers to make a homogenous compounded composition.

Disclosed herein is a method of making a compounded composition, the method comprising: mixing a therapeutically effective amount of mupirocin and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of an anti-bacterial agent and a therapeutically effective amount of itraconazole with an excipient base powder comprising a blend of micronized xylitol and poloxamers to make a homogenous compounded composition.

Disclosed herein is a method of making a compounded composition, the method comprising: mixing a therapeutically effective amount of azithromycin and a therapeutically effective amount of fluconazole with an excipient base powder comprising a blend of micronized xylitol and poloxamers to make a homogenous compounded composition.

Disclosed herein is a method of making a compounded composition, the method comprising: mixing a therapeutically effective amount of azithromycin and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of an anti-bacterial agent and a therapeutically effective amount of fluconazole with an excipient base powder comprising a blend of micronized xylitol and poloxamers to make a homogenous compounded composition.

Disclosed herein is a method of making a compounded composition, the method comprising: mixing a therapeutically effective amount of azithromycin and a therapeutically effective amount of fluconazole with an excipient base powder comprising a blend of micronized xylitol and poloxamers to make a homogenous compounded composition, and encapsulating the homogenous ccmpounded composition in one or more capsules.

Disclosed herein is a method of making a compounded composition, the method comprising: mixing a therapeutically effective amount of mupirocin and a therapeutically effective amount of nystatin with an excipient base powder comprising a blend of micronized xylitol and poloxamers to make a homogenous compounded composition.

Disclosed herein is a method of making a compounded composition, the method comprising: mixing a therapeutically effective amount of mupirocin and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of an anti-bacterial agent and a therapeutically effective amount of nystatin with an excipient base powder comprising a blend of micronized xylitol and poloxamers to make a homogenous compounded composition.

Disclosed herein is a method of treating or preventing an infection, the method comprising: (i) adding a compounded composition to water contained within a foot bath; (ii) agitating the water contained within the foot bath; and (iii) contacting the agitated water with at least a part of one or both feet of a subject.

Disclosed herein is a method of treating or preventing an infection, the method comprising: (i) mixing a compounded composition with a diluent to create a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding a compounded composition comprising an anti-bacterial agent and an anti-fungal agent to water contained within a foot bath; (ii) agitating the water contained within the foot bath; and (iii) contacting the agitated water with at least a part of one or both feet of a subject.

Disclosed herein is a method of treating or preventing an infection, the method comprising: (i) mixing a compounded composition comprising an anti-bacterial agent and an anti-fungal agent with a diluent to create a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding a compounded composition comprising mupirocin and itraconazole to water contained within a foot bath; (ii) agitating the water contained within the foot bath; and (iii) contacting the agitated water with at least a part of one or both feet of a subject.

Disclosed herein is a method of treating or preventing an infection, the method comprising: (i) mixing a compounded composition comprising mupirocin and itraconazole with a diluent to create a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding a compounded composition comprising azithromycin and fluconazole to water contained within a foot bath; (ii) agitating the water contained within the foot bath; and (iii) contacting the agitated water with at least a part of one or both feet of a subject.

Disclosed herein is a method of treating or preventing an infection, the method comprising: (i) mixing a compounded composition comprising azithromycin and fluconazole with a diluent to create a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding a compounded composition comprising mupirocin and nystatin to water contained within a foot bath; (ii) agitating the water contained within the foot bath; and (iii) contacting the agitated water with at least a part of one or both feet of a subject.

Disclosed herein is a method of treating or preventing an infection, the method comprising: (i) mixing a compounded composition comprising mupirocin and nystatin with a diluent to create a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding one or more powders to water contained within a foot bath; (ii) agitating the water contained within the foot bath; and (iii) contacting the agitated water with at least a part of one or both feet of a subject.

Disclosed herein is a method of treating or preventing an infection, the method comprising: (i) adding an anti-bacterial agent to water contained within a foot bath; (ii) adding an anti-fungal agent to the water, (iii) agitating the water contained within the foot bath; and (iv) contacting the agitated water with at least a part of one or both feet of a subject.

Disclosed herein a method of treating or preventing an infection, the method comprising: (i) mixing an anti-bacterial agent, an anti-fungal agent, and a diluent to form a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding mupirocin to water contained within a foot bath; (ii) adding an itraconazole to the water, (iii) agitating the water contained within the foot bath; and (iv) contacting the agitated water with at least a part of one or both feet of a subject.

Disclosed herein a method of treating or preventing an infection, the method comprising: (i) mixing mupirocin, itraconazole, and a diluent to form a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding azithromycin to water contained within a foot bath; (ii) adding fluconazole to the water, (iii) agitating the water contained within the foot bath; and (iv) contacting the agitated water with at least a part of one or both feet of a subject.

Disclosed herein a method of treating or preventing an infection, the method comprising: (i) mixing azithromycin, fluconazole, and a diluent to form a solution; (ii) adding the solution to water contained within a foot bath; (iii) agitating the water contained within the foot bath; and (iv) contacting the agitated water with at least part of one or both feet of a subject.

Disclosed herein is a method of treating or preventing an infection, the method comprising: (i) adding mupirocin to water contained in a foot bath, (ii) adding nystatin to the water, (iii) agitating the water contained within the foot bath; and (iv) contacting the agitated water with at least a part of one or both feet of a subject.

Disclosed herein is a method of treating or preventing an infection, the method comprising: (i) adding mupirocin to a mixing container, (ii) adding nystatin to the mixing container, (iii) adding a diluent to the mixing container, (iv) mixing the mupirocin, nystatin, and diluent in the mixing container to form a solution, (v) adding the solution to water contained within a foot bath; (vi) agitating the water contained within the foot bath; and (vii) contacting the agitated water with at least a part of one or both feet of a subject.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. For example, in an aspect, a disclosed method can optionally comprise one or more additional steps, such as, for example, repeating an administering step or altering an administering step.

As used herein, the term "capsule" includes a soft or hard shell capsule. A capsule shell can be a unibody delivery vehicle or can be comprised of two capsule shell pieces. In an aspect, the longer capsule shell piece can be called the "body" and the smaller capsule shell piece can be called the "cap". The body and the cap can engage with each other as one shell body. As known to the art, capsule sizes can differ considering various factors that are tailored for any particular application, such as dosage amount or route of administration. Capsules can be manufactured to achieve a variety of capsule shell thicknesses. The release characteristics of a capsule can vary depending on the capsule shell thickness and composition. Standard capsule sizes are known in the art, and include, but are not limited to, the following sizes: Su07 (~28 mL), 7 (~24 mL), 10 (~18 mL), 11 (~10 mL), 12el (~7.5 mL), 12 (~5 mL), 13 (~3.2 mL), 000 (~1.37 mL), 00 (~0.95 mL), 0 (~0.68 mL), 1 (~0.50 mL), 2 (~0.37 mL), 3 (~0.30 mL), 4 (~0.21 mL), and 5 (~0.13 mL). Actual volumes in mL are shown in parenthesis. Capsules for oral administration typically range from a size 5 (volume of 0.1 mL) capsule to a size 000 (volume of 1.37 mL) capsule.

The capacity of a capsule measures how much of a disclosed compounded composition or a disclosed agent that a capsule can hold or contain. The capacity of a capsule depends largely on the density of the composition (compositions and anti-infective agents vary widely in density). A capsule can hold less of a composition or an anti-infective agent with a low density (i.e., around 0.6 g/mL) and can hold more of a composition or an agent having a high density (i.e., 1.2 g/mL). The table below shows the approximate capacity (in milligrams) of various capsules (e.g., capsule size 000 to capsule size 4) across a range of densities for a disclosed compounded composition or a disclosed anti-infective agent (i.e., an anti-bacterial agent or an anti-fungal agent).

| Powder Density | Capacity (mg) for Various Capsule Sizes | | | | | | |
|---|---|---|---|---|---|---|---|
| | 000 | 00 | 0 | 1 | 2 | 3 | 4 |
| 0.6 g/ml | 822 | 570 | 408 | 288 | 216 | 162 | 120 |
| 0.8 g/ml | 1096 | 760 | 544 | 384 | 288 | 216 | 160 |
| 1.0 g/ml | 1370 | 950 | 680 | 480 | 360 | 270 | 200 |
| 1.2 g/ml | 1644 | 1140 | 816 | 576 | 432 | 324 | 240 |

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient. A subject can have diabetes. A subject can be obese. A subject can have circulatory issues. A subject can have a bacterial infection, be suspected of having a bacterial infection, or be at risk of developing a bacterial infection. A subject can have a fungal infection, be suspected of having a fungal infection, or be at risk of developing a fungal infection. For example, a subject can have damaged or moist skin, can have chronic disease, or can be immunocompromised. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

A "patient" refers to a subject afflicted with one or more diseases or disorders. In an aspect, a patient can refer to a subject that has been diagnosed with or is suspected of having a fungal infection. In an aspect, a patient can refer to a subject that has been diagnosed with or is suspected of having a bacterial infection. In an aspect, a bacterial infection or suspected bacterial infection can affect at least a portion of one or both feet of the subject. In an aspect, a bacterial infection or suspected bacterial infection can affect another appendage, such as at least a portion of one or both of the subject's hands. In an aspect, a fungal infection or suspected fungal infection can affect at least a portion of one or both feet of the subject. In an aspect, a fungal infection or suspected fungal infection can affect another appendage, such as at least a portion of one or both of the subject's hands.

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

In an aspect, "treating" means eradicating a bacterial infection, a fungal infection, a suspected bacterial infection, a suspected fungal infection, or a combination thereof. In an aspect, "treating" means reducing the effects of a bacterial infection or fungal infection or symptoms of a bacterial infection or a fungal infection. Thus, in an aspect of a disclosed method, treating can refer to a 10%, 20%, 30%, 40%, 50%, 60%, 70%, 80%, 90%, or 100% reduction in the severity of an established bacterial infection or an established fungal infection or in the symptoms of a bacterial infection or a fungal infection. For example, a method for treating a bacterial infection or fungal infection can reduce one or more symptoms of a bacterial infection, a fungal infection, or both in a subject by 10% as compared to a control. In an aspect, a reduction of one or more symptoms can be 20%, 30%, 40%, 50%, 60%, 70%, 80%, 90%, 100%, or any percent reduction in between 10% and 100% as compared to a control. It is understood that treatment does not necessarily refer to a cure or complete ablation or eradication of the bacterial infection or the fungal infection, or both. However, in an aspect, treatment can refer to a cure or complete ablation or eradication of the bacterial infection, the fungal infection, or both.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In an aspect, preventing a bacterial infection, fungal infection, or both is intended.

As used herein, the term "diagnosed" means having been subjected to a physical examination by a person of skill, for example, a physician, and found to have a condition that can be diagnosed or treated by the compounds, compositions, agents, or methods disclosed herein. For example, "diagnosed with a bacterial infection" means having been subjected to a physical examination by a person of skill, for example, a physician, and found to have a condition that can be diagnosed or can be treated by a disclosed compound or composition or agent that can prevent or inhibit a bacterial infection. For example, "suspected of having a bacterial infection" can mean having been subjected to a physical examination by a person of skill, for example, a physician, and found to have a condition that can be likely be diagnosed as or can likely be treated by a disclosed compound or composition or agent that can prevent or inhibit a bacterial infection, or it can mean that the subject believes that he or she has a bacterial infection. For example, "diagnosed with a fungal infection" means having been subjected to a physical examination by a person of skill, for example, a physician, and found to have a condition that can be diagnosed or can be treated by a disclosed compound or composition or agent that can prevent or inhibit a fungal infection. For example, "suspected of having a fungal infection" can mean having been subjected to a physical examination by a person of skill, for example, a physician, and found to have a condition that can be likely be diagnosed as or can likely be treated by a disclosed compound or composition or agent that can prevent or inhibit a fungal infection, or it can mean that the subject believes that he or she has a fungal infection.

As used herein, the terms "administering" and "administration" refer to any method of providing a disclosed composition, compounded composition, anti-infective agent, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed composition, compounded composition, or anti-infective agent can be administered therapeutically; that is, administered to treat an existing disease or condition. In further various aspects, a disclosed composition, compounded composition, or anti-infective agent can be administered prophylactically; that is, administered for prevention of a disease or condition. In an aspect, the skilled person can determine an efficacious dose, an efficacious schedule, and an efficacious route of administration for a disclosed composition, compounded composition, or anti-infective agent so as to treat a subject or inhibit or prevent an inflammatory reaction. In an aspect, the skilled person can also alter, change, or modify an aspect of an administering step so as to improve efficacy of a disclosed composition, compounded composition, or anti-infective agent. In an aspect, administering means contacting at least a portion of one foot or both feet of a subject with agitated water comprising a disclosed composition, compounded composition, or anti-infective agent in a foot bath.

As used herein, a "foot bath" refers to a container that can hold some volume (e.g., about 15 liters to about 30 liters) of aqueous solution (e.g., water) and is designed to physically accommodate at least a portion of one or both feet of a subject. Foot baths are known to the skilled person. A foot bath can comprise several features or agents that effect various functions. For example, a foot bath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or feet of the subject, a massage agent (e.g., a roller) that provides massaging contact to at least a portion of one or both feet, a pedicure agent that can clean or contact a foot or feet with a pumice, or a combination thereof. In an aspect, an agitation agent or an agitator can be coupled to both a motor and the foot bath. Motors and agitators are known to the art. In an aspect, a foot bath can comprise one or more splash guards and other spill-resistant features to ensure that the water remains enclosed within a container. A foot bath may also accommodate a subject's calves, meaning that the container is "deep" so as to allow the enclosed water to contact both the feet and at least a portion of the calves of the subject. Several manufacturers market foot baths including PIBB, Dr. Scholl's, Kendal, Conair, and Brookstone.

As used herein, a "scoop" refers to tool that can be used to measure or dispense a disclosed a compounded composition, a disclosed powder, or a disclosed anti-infective agent. In an aspect, a scoop can have a pre-determined size that can measure a pre-determined amount. In an aspect, a scoop can measure or dispense an amount of about 1 g to about 10 g. In an aspect, a scoop can measure about 1 g, about 2 g, about 3 g, about 4 g, about 5 g, about 6 g, about 7 g, about 8 g, about 9 g, or about 10 g. In an aspect, a scoop can measure or dispense an amount of 10 g or more. For example, in an aspect, a scoop can measure or dispense an amount of about 1 mg to about 1 g. In an aspect, a scoop can measure about 1 mg, about 100 mg, about 200 mg, about 300 mg, about 400 mg, about 500 mg, about 600 mg, about 700 mg, about 800 mg, about 900 g, or about 1 g. In an aspect, a scoop can measure or dispense an amount of about 250 mg. In an aspect, a scoop can measure or dispense an amount of about 500 mg. In an aspect, a scoop can measure or dispense an amount of about 1.5 g.

As used herein, a "scoop" can also refer to tool that can be used to measure or dispense a disclosed diluent. In an aspect, a scoop can have a pre-determined size that can measure a pre-determined volume. For example, in an aspect, a scoop can measure or dispense a volume of about 1 mL to about 30 mL. In an aspect, a scoop can measure about 1 mL, about 2 mL, about 3 mL, about 4 mL, about 5 mL, about 6 mL, about 7 mL, about 8 mL, about 9 mL, about 10 mL, about 15 mL, about 20 mL, about 25 mL, or about 30 mL. In an aspect, a scoop can measure or dispense an amount of 10 mL or more. In an aspect, a scoop can measure or dispense an amount of about 15 mL.

As used herein, a "mixing container" can be a container that can accommodate one more liquids (such as a diluent, for example) and one or more disclosed compositions or disclosed anti-infective agents. A mixing container can have a lid or a cover, which facilitates the mixing of any liquid with any solid that has been added to the container. A mixing container can be used to generate a solution. In an aspect, a mixing container can contain an amount from about 2 ounces to about 30 ounces. In an aspect, a mixing container can contain an amount of about 6 ounces. In an aspect, a mixing container can contain an amount of about 16 ounces. The art is familiar with mixing containers and mixing containers are commercially available.

As used herein, "modifying the method" can comprise modifying or changing one or more features or aspects of one or more steps of a disclosed method. For example, in an aspect, a method can be altered by changing the amount of a disclosed compounded composition, a disclosed composition, or a disclosed anti-infective agent added to a foot bath, by changing the frequency of the subject's use of the foot bath, or by changing the duration of time that the subject's foot or feet contact the water contained within the foot bath, or a combination thereof.

As used herein, poloxamers are non-ionic poly (ethylene oxide) (PEO)-poly (propylene oxide) (PPO) copolymers. Poloxamers can be used in pharmaceutical formulations as surfactants, emulsifying agents, solubilizing agent, dispersing agents, and in vivo absorbance enhancer. Poloxamers are often considered as "functional excipients" because they are essential components, and play an important role in the formulation. Poloxamers are synthetic triblock copolymers with the following formula:

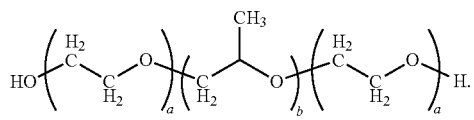

The term "contacting" as used herein refers to bringing one or more disclosed compositions, disclosed compounded compositions, or disclosed anti-infective agents together with water and an intended target (such as at least a portion of one or both feet of a subject) or targeted area (such as an area diagnosed with, suspected of having a bacterial infection or a fungal infection, or susceptible to developing a bacterial infection or a fungal infection) in such a manner that the disclosed composition, a disclosed compounded composition, or a disclosed anti-infective agent can exert an effect on the intended target or targeted area either directly or indirectly. In an aspect, "contacting" means to insert or immerse at least a portion of one or both feet of a subject into the water contained within a foot bath.

The term "mixing" as used in a disclosed method of making a compounded composition, for example, means to physically combine the recited components so as to achieve a homogenous compounded composition (which can be a dry powder formulation). For example, in an aspect, an anti-bacterial agent and an anti-fungal agent can be mixed with an excipient base powder; that is, an anti-bacterial agent and an anti-fungal agent are physically combined with an excipient base powder and shaken, or stirred, or agitated so as to achieve a homogenous compounded composition. In an aspect, multiple recited components can be mixed together (i.e., anti-bacterial agent, an anti-fungal agent, an excipient base powder, and one or more additional anti-infective agents (i.e., anti-bacterial agent and anti-fungal agent). In an aspect, "mixing" can also include sifting the homogenous compounded composition though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogenous compounded composition.

Also, in an aspect, "mixing" can be used to describe the process of making a solution by adding one or more of a disclosed compounded composition, a disclosed composition, or a disclosed anti-infective agent to a diluent. For example, mixing means to physically combine one or more of a disclosed compounded composition, a disclosed composition, or a disclosed anti-infective agent with a diluent.

"Mixing" can occur in a disclosed mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, mixing container can measure or hold about 1 ounce, 2 ounces, 3 ounces, 4 ounces, 5 ounces, 6 ounces, 7 ounces, 8 ounces, 9 ounces, 10 ounces, 11 ounces, 12 ounces, 13 ounces, 14 ounces, 15 ounces, 16 ounces, 17 ounces, 18 ounces, 19 ounces, 20 ounces, 21 ounces, 22 ounces, 23 ounces, 24 ounces, 25 ounces, 26 ounces, 27 ounces, 28 ounces, 29 ounces, or 30 ounces. In an aspect, a mixing container can measure or hold about 6 ounces. In an aspect, a mixing container can measure or hold about 16 ounces.

As used herein, an anti-infective agent can be an anti-bacterial agent, an anti-fungal agent, a combination of anti-bacterial agents, a combination of anti-fungal agents, or a combination of anti-bacterial agents and anti-fungal agents.

Anti-bacterial agents are known to the art. For example, the art generally recognizes several categories of anti-bacterial agents including (1) enicillins, (2) cephalosporins, (3) fluoroquinolones, (4) aminoglycosides, (5) monobactams, (6) carbapenems, (7) macrolides, and (8) other agents. For example, as used herein, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

Anti-fungal agents are known to the art. The art generally recognizes several categories of anti-fungal agents including (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents. For example, as used herein, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

Mupirocin is an anti-bacterial agent that has excellent activity against gram-positive staphylococci and streptococci. Mupirocin is used primarily for the treatment of primary and secondary skin disorders, nasal infections, and wound healing. Mupirocin inhibits bacterial protein synthesis by specific reversible binding to bacterial isoleucyl tRNA synthase. The molecular formula for mupirocin is $C_{26}H_{44}O_9$. Mupirocin is shown below.

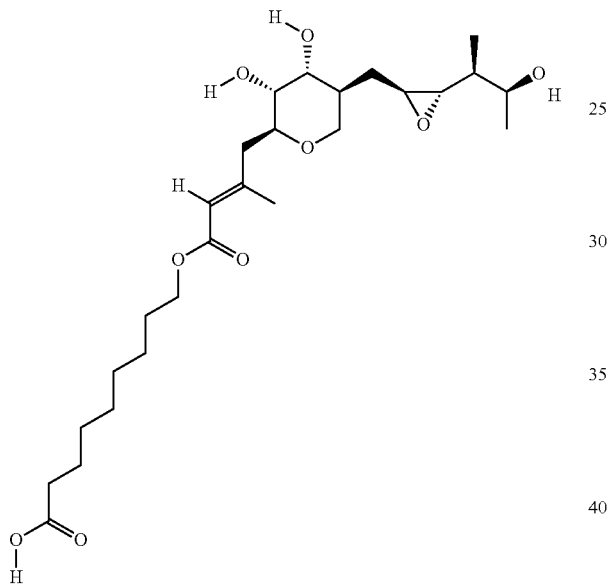

Azithromycin is a semi-synthetic macrolide antibiotic structurally related to erythromycin. It has been used in the treatment of *Mycobacterium avium intracellulare* infections, toxoplasmosis, and cryptosporidiosis. The molecular formula for azithromycin is $C_{38}H_{72}N_2O_{12}$. Azithromycin is shown below.

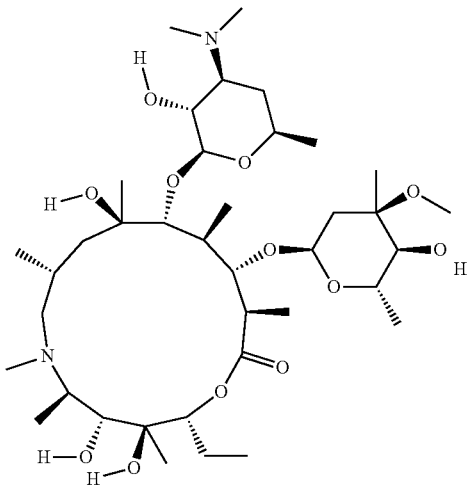

Itraconazole is a synthetic triazole antifungal agent that inhibits cytochrome P-450-dependent enzymes required for ergosterol synthesis. Itraconazole has antimycotic properties. Formulated for both topical and systemic use, itraconazole preferentially inhibits fugal cytochrome P450 enzymes, resulting in a decrease in fungal ergosterol synthesis. Because of its low toxicity profile, this agent can be used for long-term maintenance treatment of chronic fungal infections. The molecular formula for itraconazole is $C_{35}H_{38}C_{12}N_8O_4$. Itraconazole is shown below.

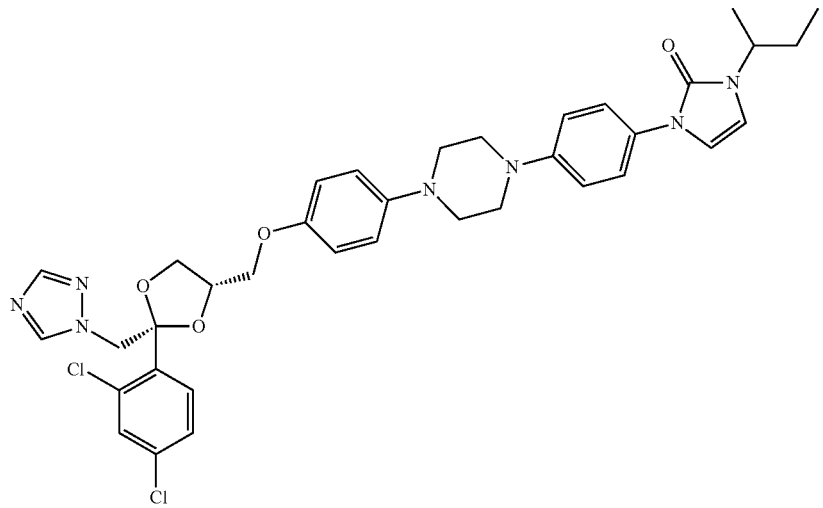 [SMILES: CCC(C)n1ccn(-c2ccc(N3CCN(c4ccc(OC[C@H]5CO[C@](Cn6cncn6)(c6ccc(Cl)cc6Cl)O5)cc4)CC3)cc2)c1=O]

Fluconazole is a synthetic triazole with antifungal activity. Fluconazole preferentially inhibits fungal cytochrome P450 sterol C-14 alpha-demethylation, resulting in the accumulation of fungal 14 alpha-methyl sterols, the loss of normal fungal sterols, and fungistatic activity. Mammalian cell demethylation is much less sensitive to fluconazole inhibition. The mechanism of action of fluconazole is as a cytochrome P450 2C19 inhibitor, cytochrome P450 3A4 inhibitor, and cytochrome P450 2C9 inhibitor. The molecular formula for fluconazole is $C_{13}H_{12}F_2N_6O$. Fluconazole is shown below.

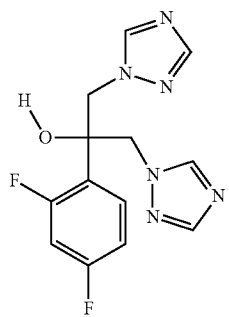 [SMILES: OC(Cn1cncn1)(Cn1cncn1)c1ccc(F)cc1F]

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various anti-bacterial and anti-fungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, "determining" can refer to measuring or ascertaining the presence and severity of an infection, such as, for example, a bacterial infection or a fungal infection that affects one or more of a subject's appendages (e.g., at least a portion of one or both feet). Methods and techniques used to determining the presence and/or severity of an infection are typically known to the medical arts. For example, the art is familiar with the ways to identify and/or diagnose the presence, severity, or both of a bacterial infection, a fungal infection, or both.

As used herein, "effective amount" and "amount effective" can refer to an amount that is sufficient to achieve the desired result such as, for example, the treatment and/or prevention of a bacterial infection or a suspected bacterial infection or a fungal infection or a suspected fungal infection. As used herein, the terms "effective amount" and "amount effective" can refer to an amount that is sufficient to achieve the desired an effect on an undesired condition (e.g., a bacterial or fungal infection). For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, then the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition, such as, for example, a bacterial infection or a fungal infection.

As used herein, LoxaSperse™ refers to an excipient base powder comprising a blend of micronized xylitol and poloxamers. LoxaSperse™ is used as a chemical dispersing or solubilizing agent, thereby improving the solubility and dispersibility of poorly water soluble active pharmaceutical ingredients (APIs) or agents. LoxaSperse™ can be obtained from a bulk source.

As used herein, XyliFos™ refers to an excipient base powder comprising xylitol, poloxamer 407, hydroxylpropyl betadex, and epigallocatechin gallate. XyliFos™ is used as a chemical dispersing or solubilizing agent, thereby improving the solubility and dispersibility of poorly water soluble active pharmaceutical ingredients (APIs) or agents. In an aspect, infectious agents such as bacteria and fungi can consume or uptake XyliFos™, but cannot digest, process, or excrete XyliFos™. This leads to the infectious agent's death. XyliFos™ can be obtained from a bulk source. In an aspect, Xylifos As described herein, the combined use of LoxaSperse and XyliFos can improve the efficiency and performance of the disclosed compounded composition as XyliFos improves the solubilizing and dispensing characteristics of LoxaSperse.

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Compounded Compositions

Disclosed herein is a compounded composition for treating an infection.

1. Compounded Composition Comprising an Anti-Bacterial Agent and an Anti-Fungal Agent Disclosed herein can be a compounded composition comprising an anti-bacterial agent, an anti-fungal agent, and an excipient base powder comprising a blend of micronized xylitol and poloxamers.

In an aspect, the compounded composition can be a dry powder formulation. In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the anti-fungal agent can be a dry powder. In an aspect, the anti-fungal agent can be an ointment. The anti-fungal agent can be pure or substantially pure. The anti-fungal agent can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise from about 10% to about 40% w/w of the compounded composition. In an aspect, the anti-bacterial agent can comprise from about 15% to about 35% w/w of the compounded composition. In an aspect, the anti-bacterial agent can comprise from about 20% to about 30% w/w of the compounded composition. In an aspect, the anti-bacterial agent can comprise about 25% w/w of the compounded composition.

In an aspect, the anti-fungal agent can comprise from about 10% to about 40% w/w of the compounded composition. In an aspect, the anti-fungal agent can comprise from about 15% to about 35% w/w of the compounded composition. In an aspect, the anti-fungal agent can comprise from about 20% to about 30% w/w of the compounded composition. In an aspect, the anti-fungal agent can comprise about 25% w/w of the compounded composition.

In an aspect, the ratio of the anti-bacterial agent to the anti-fungal agent in the compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1.25:1. For example, Table 1 presents a representative, but not exhaustive, listing of the % w/w of the components of a disclosed compounded composition.

TABLE 1

REPRESENTATIVE LISTING OF COMPONENTS (% W/W) IN A COMPOUNDED COMPOSITION

| Anti-Bacterial | Anti-Fungal | Loxasperse and/or Xylifos |
|---|---|---|
| 10 | 10-40 | qS |
| 15 | 10-40 | qS |
| 20 | 10-40 | qS |
| 25 | 10-40 | qS |
| 30 | 10-40 | qS |
| 35 | 10-40 | qS |
| 40 | 10-40 | qS |
| 10-40 | 10 | qS |
| 10-40 | 15 | qS |
| 10-40 | 20 | qS |
| 10-40 | 25 | qS |
| 10-40 | 30 | qS |
| 10-40 | 35 | qS |
| 10-40 | 40 | qS |
| 10 | 10 | 80 |
| 15 | 15 | 70 |
| 20 | 20 | 60 |
| 25 | 25 | 50 |
| 30 | 30 | 40 |
| 35 | 35 | 30 |
| 40 | 40 | 20 |

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect, the anti-bacterial agent can comprise mupirocin. In an aspect, the anti-bacterial agent can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect, the anti-fungal agent can comprise itraconazole. In an aspect, the anti-fungal agent can comprise fluconazole. In an aspect, the anti-fungal agent can comprise nystatin.

In an aspect of a disclosed compounded composition, the anti-bacterial agent can comprise mupirocin and the anti-fungal agent can comprise itraconazole. In an aspect of a disclosed compounded composition, the anti-bacterial agent can comprise azithromycin and the anti-fungal agent can comprise fluconazole. In an aspect of a disclosed compounded composition, the anti-bacterial agent can comprise mupirocin and the anti-fungal agent can comprise nystatin. In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising an anti-bacterial agent and an anti-fungal agent can be encapsulated in one or more capsules. The art is familiar with capsules, methods of making capsules, and methods of using capsules to encapsulate one or more disclosed compositions or one or more disclosed agents.

2. Compounded Composition Comprising Mupirocin and an Anti-Fungal Agent

Disclosed herein is a compounded composition comprising mupirocin, an anti-fungal agent, and an excipient base powder comprising a blend of micronized xylitol and poloxamers.

In an aspect, the compounded composition can be a dry powder formulation.

In an aspect, the mupirocin can be a dry powder. In an aspect, the mupirocin can be an ointment. The mupirocin can be pure or substantially pure. The mupirocin can be obtained from a bulk source. In an aspect, the anti-fungal agent can be a dry powder. In an aspect, the anti-fungal agent can be an ointment. The anti-fungal agent can be pure or substantially pure. The anti-fungal agent can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. The anti-fungal agent can comprise itraconazole.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the anti-fungal agent can comprise from about 10% to about 40% w/w of the compounded composition. In an aspect, the anti-fungal agent can comprise from about 15% to about 35% w/w of the compounded composition. In an aspect, the anti-fungal agent can comprise from about 20% to about 30% w/w of the compounded composition. In an aspect, the anti-fungal agent can comprise about 25% w/w of the compounded composition.

In an aspect, the ratio of the mupirocin to the anti-fungal agent in the compounded composition can be from about 1:4 to about 4:1. In an aspect, the ratio of the mupirocin to the anti-fungal agent can be about 1:1. In an aspect, the ratio of the mupirocin to the anti-fungal agent can be about 1.25:1. See, e.g., Table 1.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising mupirocin and an anti-fungal agent can be encapsulated in one or more capsules. The art is familiar with capsules, methods of making capsules, and methods of using capsules to encapsulate one or more disclosed compositions or one or more disclosed agents.

3. Compounded Composition Comprising an Anti-Bacterial Agent and Itraconazole

Disclosed herein is a compounded composition comprising an anti-bacterial agent, itraconazole, and an excipient base powder comprising a blend of micronized xylitol and poloxamers.

In an aspect, the compounded composition can be a dry powder formulation.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the itraconazole can be a dry powder. In an aspect, the itraconzazole can be an ointment. The itraconazole can be pure or substantially pure. The itraconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise from about 10% to about 40% w/w of the compounded composition. In an aspect, the anti-bacterial agent can comprise from about 15% to about 35% w/w of the compounded composition. In an aspect, the anti-bacterial agent can comprise from about 20% to about 30% w/w of the compounded composition. In an aspect, the anti-bacterial agent can comprise about 25% w/w of the compounded composition.

In an aspect, the itraconazole can comprise from about 10% to about 40% w/w of the compounded composition. In an aspect, the itraconazole can comprise from about 15% to about 35% w/w of the compounded composition. In an aspect, the itraconazole can comprise from about 20% to about 30% w/w of the compounded composition. In an aspect, the itraconazole can comprise about 25% w/w of the compounded composition.

In an aspect, the ratio of the anti-bacterial agent to the itraconazole in the compounded composition can be from about 1:4 to about 4:1. In an aspect, the ratio of the anti-bacterial agent to the itraconazole can be about 1:1. In an aspect, the ratio of the anti-bacterial agent to the itraconazole can be about 1.25:1. See, e.g., Table 2.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising an anti-bacterial agent and itraconazole can be encapsulated in one or more capsules. The art is familiar with capsules, methods of making capsules, and methods of using capsules to encapsulate one or more disclosed compositions or one or more disclosed agents.

4. Compounded Composition Comprising Mupirocin and Itraconazole

Disclosed herein is a compounded composition comprising mupirocin, itraconazole, and an excipient base powder comprising a blend of micronized xylitol and poloxamers.

In an aspect, the compounded composition can be a dry powder formulation.

In an aspect, the mupirocin can be a dry powder. In an aspect, the mupirocin can be an ointment. The mupirocin can be pure or substantially pure. The mupirocin can be obtained from a bulk source. In an aspect, the itraconazole can be a dry powder. In an aspect, the itraconazole can be an ointment. The itraconazole can be pure or substantially pure. The itraconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the itraconazole can comprise from about 10% to about 40% w/w of the compounded composition. In an aspect, the itraconazole can comprise from about 15% to about 35% w/w of the compounded composition. In an aspect, the itraconazole can comprise from about 20% to about 30% w/w of the compounded composition. In an aspect, the itraconazole can comprise about 25% w/w of the compounded composition.

In an aspect, the ratio of the mupirocin to the itraconazole in the compounded composition can be from about 1:4 to about 4:1. In an aspect, the ratio of the mupirocin to the itraconazole can be about 1:1. In an aspect, the ratio of the mupirocin to the itraconazole can be about 1.25:1. See, for example, Table 2, which presents a representative, but not exhaustive, listing of the % w/w of mupirocin and itraconazole in a disclosed compounded composition.

TABLE 2

REPRESENTATIVE LISTING OF MUPIROCIN AND ITRACONAZOLE (% W/W) IN A COMPOUNDED COMPOSITION

| Mupirocin | Itraconazole | Loxasperse and/or Xylifos (%) |
| --- | --- | --- |
| 10 | 10-40 | qS |
| 15 | 10-40 | qS |
| 20 | 10-40 | qS |
| 25 | 10-40 | qS |
| 30 | 10-40 | qS |

TABLE 2-continued

REPRESENTATIVE LISTING OF MUPIROCIN
AND ITRACONAZOLE (% W/W) IN A
COMPOUNDED COMPOSITION

| Mupirocin | Itraconazole | Loxasperse and/or Xylifos (%) |
|---|---|---|
| 35 | 10-40 | qS |
| 40 | 10-40 | qS |
| 10-40 | 10 | qS |
| 10-40 | 15 | qS |
| 10-40 | 20 | qS |
| 10-40 | 25 | qS |
| 10-40 | 30 | qS |
| 10-40 | 35 | qS |
| 10-40 | 40 | qS |
| 10 | 10 | 80 |
| 15 | 15 | 70 |
| 20 | 20 | 60 |
| 25 | 25 | 50 |
| 30 | 30 | 40 |
| 35 | 35 | 30 |
| 40 | 40 | 20 |

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising mupirocin and itraconazole can be encapsulated in one or more capsules. The art is familiar with capsules, methods of making capsules, and methods of using capsules to encapsulate one or more disclosed compositions or one or more disclosed agents.

Disclosed herein is a compounded composition comprising mupirocin, itraconazole, an excipient base powder comprising a blend of micronized xylitol and poloxamers, and at least one additional anti-infective agent.

In an aspect, the compounded composition can be a dry powder formulation.

In an aspect, the mupirocin can be obtained from a bulk source. The mupirocin can be pure or substantially pure. In an aspect, the mupirocin can be an ointment. In an aspect, the itraconazole can be obtained from a bulk source. In an aspect, the itraconazole can be an ointment. The itraconazole can be pure or substantially pure. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the itraconazole can comprise from about 10% to about 40% w/w of the compounded composition. In an aspect, the itraconazole can comprise from about 15% to about 35% w/w of the compounded composition. In an aspect, the itraconazole can comprise from about 20% to about 30% w/w of the compounded composition. In an aspect, the itraconazole can comprise about 25% w/w of the compounded composition.

In an aspect, the ratio of the mupirocin to the itraconazole in the compounded composition can be from about 1:4 to about 4:1. In an aspect, the ratio of the mupirocin to the itraconazole can be about 1:1. In an aspect, the ratio of the mupirocin to the itraconazole can be about 1.25:1. See, e.g., Table 2.

In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising mupirocin, itraconazole, and at least one additional anti-infective agent can be encapsulated in one or more capsules. The art is familiar with capsules, methods of making capsules, and methods of using capsules to encapsulate one or more disclosed compositions or one or more disclosed agents.

5. Compounded Composition Comprising Azithromycin and an Anti-Fungal Agent

Disclosed herein is a compounded composition comprising azithromycin, an anti-fungal agent, and an excipient base powder comprising a blend of micronized xylitol and poloxamers.

In an aspect, the compounded composition can be a dry powder formulation.

In an aspect, the azithromycin can be a dry powder. In an aspect, the azithromycin can be an ointment. The azithromycin can be pure or substantially pure. The azithromycin can be obtained from a bulk source. In an aspect, the anti-fungal agent can be a dry powder. In an aspect, the anti-fungal agent can be an ointment. The anti-fungal agent can be pure or substantially pure. The anti-fungal agent can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the anti-fungal agent can comprise from about 10% to about 60% w/w of the compounded composition. In an aspect, the anti-fungal agent can comprise from about 20% to about 50% w/w of the compounded composition. In an aspect, the anti-fungal agent can comprise from about 30% to about 40% w/w of the compounded composition. In an aspect, the anti-fungal agent can comprise about 25% w/w of the compounded composition. In an aspect, the anti-fungal agent can comprise about 50% w/w of the compounded composition.

In an aspect, the ratio of the azithromycin to the anti-fungal agent in the compounded composition can be from about 1:4 to about 4:1. In an aspect, the ratio of the azithromycin to the anti-fungal agent can be about 1:1. In an aspect, the ratio of the azithromycin to the anti-fungal agent can be about 1.25:1.

In an aspect, anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect, the anti-fungal agent can comprise fluconazole.

In an aspect, a disclosed compounded composition comprising azithromycin and an anti-fungal agent can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising azithromycin and an anti-fungal agent can be encapsulated in one or more capsules. The art is familiar with capsules, methods of making capsules, and methods of using capsules to encapsulate one or more disclosed compositions or one or more disclosed agents.

6. Compounded Composition Comprising an Anti-Bacterial Agent and Fluconazole

Disclosed herein is a compounded composition comprising an anti-bacterial agent, fluconazole, and an excipient base powder comprising a blend of micronized xylitol and poloxamers.

In an aspect, the compounded composition can be a dry powder formulation.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the fluconazole can be a dry powder. In an aspect, the fluconazole can be an ointment. The fluconazole can be pure or substantially pure. The fluconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise from about 10% to about 60% w/w of the compounded composition. In an aspect, the anti-bacterial agent can comprise from about 20% to about 50% w/w of the compounded composition. In an aspect, the anti-bacterial agent can comprise from about 30% to about 40% w/w of the compounded composition. In an aspect, the anti-bacterial agent can comprise about 25% w/w of the compounded composition. In an aspect, the anti-bacterial agent can comprise about 50% w/w of the compounded composition.

In an aspect, the fluconazole agent can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the anti-bacterial agent to the fluconazole in the compounded composition can be from about 1:4 to about 4:1. In an aspect, the ratio of the anti-bacterial agent to the fluconazole can be about 1:1. In an aspect, the ratio of the anti-bacterial agent to the fluconazole can be about 1.25:1.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect, the anti-bacterial agent can comprise azithromycin.

In an aspect, a disclosed compounded composition comprising an anti-bacterial agent and fluconazole can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising an anti-bacterial agent and fluconazole can be encapsulated in one or more capsules. The art is familiar with capsules, methods of making capsules, and methods of using capsules to encapsulate one or more disclosed compositions or one or more disclosed agents.

7. Compounded Composition Comprising Azithromycin and Fluconazole

Disclosed herein is a compounded composition comprising azithromycin, fluconazole, and an excipient base powder comprising a blend of micronized xylitol and poloxamers.

In an aspect, the compounded composition can be a dry powder formulation.

In an aspect, the azithromycin can be a dry powder. In an aspect, the azithromycin can be an ointment. The azithromycin can be pure or substantially pure. The azithromycin can be obtained from a bulk source. In an aspect, the fluconazole can be a dry powder. In an aspect, the fluconazole can be an ointment. The fluconazole can be pure or substantially pure. The fluconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the fluconazole can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the azithromycin to the fluconazole in the compounded composition can be from about 1:4 to about 4:1. In an aspect, the ratio of the azithromycin to the fluconazole can be about 1:1. In an aspect, the ratio of the azithromycin to the fluconazole can be about 1.25:1. See, e.g., Table 3 which presents a representative, but not exhaustive, listing of the % w/w of azithromycin to fluconazole in a disclosed compounded composition.

TABLE 3

REPRESENTATIVE LISTING
OF AZITHROMYCIN AND
FLUCONAZOLE (% W/W) IN A
COMPOUNDED COMPOSITION

| Azithromycin | Fluconazole | Loxasperse and/or Xylifos (%) |
|---|---|---|
| 10 | 10-40 | qS |
| 15 | 10-40 | qS |
| 20 | 10-40 | qS |
| 25 | 10-40 | qS |
| 30 | 10-40 | qS |
| 35 | 10-40 | qS |
| 40 | 10-40 | qS |
| 10-40 | 10 | qS |
| 10-40 | 15 | qS |
| 10-40 | 20 | qS |
| 10-40 | 25 | qS |
| 10-40 | 30 | qS |
| 10-40 | 35 | qS |
| 10-40 | 40 | qS |
| 10 | 10 | 80 |
| 15 | 15 | 70 |
| 20 | 20 | 60 |
| 25 | 25 | 50 |
| 30 | 30 | 40 |
| 35 | 35 | 30 |
| 40 | 40 | 20 |

In an aspect, the compounded composition comprising azithromycin and fluconazole can comprise at least one additional anti-infective agent. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising azithromycin and fluconazole can be encapsulated in one or more capsules. The art is familiar with capsules, methods of making capsules, and methods of using capsules to encapsulate one or more disclosed compositions or one or more disclosed agents.

Disclosed herein is a compounded composition comprising azithromycin, fluconazole, an excipient base powder comprising a blend of micronized xylitol and poloxamers, and at least one additional anti-infective agent.

In an aspect, the compounded composition can be a dry powder formulation.

In an aspect, the azithromycin can be a dry powder. In an aspect, the azithromycin can be an ointment. The azithromycin can be pure or substantially pure. The azithromycin can be obtained from a bulk source. In an aspect, the fluconazole can be a dry powder. In an aspect, the fluconazole can be an ointment. The fluconazole can be pure or substantially pure. The fluconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the fluconazole can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the azithromycin to fluconazole in the compounded composition can be from about 1:4 to about 4:1. In an aspect, the ratio of the azithromycin to the fluconazole can be about 1:1. In an aspect, the ratio of the azithromycin to the fluconazole can be about 1.25:1. See, e.g., Table 3.

In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising azithromycin, fluconazole, and at least one additional anti-infective agent can be encapsulated in one or more capsules. The art is familiar with capsules, methods of making capsules, and methods of using capsules to encapsulate one or more disclosed compositions or one or more disclosed agents.

8. Compounded Composition Comprising Mupirocin and Nystatin

Disclosed herein can be a compounded composition comprising mupirocin, nystatin, and an excipient base powder comprising a blend of micronized xylitol and poloxamers.

In an aspect, the compounded composition can be a dry powder formulation.

In an aspect, the mupirocin can be obtained from a bulk source. The mupirocin can be pure or substantially pure. In an aspect, the mupirocin can be a dry powder. In an aspect, the mupirocin can be an ointment. In an aspect, the mupirocin can be a 2% ointment. In an aspect, the mupirocin can be provided in a tube. For example, in an aspect, the mupirocin can be provided in a 22 gram tube. In an aspect, the nystatin can be obtained from a bulk source. The nystatin can be pure or substantially pure. In an aspect, the nystatin can be a dry powder. In an aspect, the nystatin can be an ointment. In an aspect, the nystatin can be provided in a container. For example, in an aspect, the nystatin can be provided in 15 gram container.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the nystatin can comprise from about 10% to about 40% w/w of the compounded composition. In an aspect, the nystatin can comprise from about 15% to about 35% w/w of the compounded composition. In an aspect, the nystatin can comprise from about 20% to about 30% w/w of the compounded composition. In an aspect, the nystatin can comprise about 25% w/w of the compounded composition. In an aspect, the ratio of the mupirocin to the nystatin in the compounded composition can be from about 1:4 to about 4:1. In an aspect, the ratio of the mupirocin to the nystatin can be about 1:1 or the ratio can be about 1.5:1.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising mupirocin and nystatin can be encapsulated in one or more capsules. The art is familiar with capsules, methods of making capsules, and methods of using capsules to encapsulate one or more disclosed compositions or one or more disclosed agents.

C. Capsules

1. Capsules Comprising a Compounded Composition

Disclosed herein is a capsule comprising a disclosed compounded composition.

Disclosed herein is a capsule comprising a compounded composition, wherein the compounded composition comprises an anti-bacterial agent and an anti-fungal agent.

Disclosed herein is a capsule comprising a compounded composition, wherein the compounded composition comprises an anti-bacterial agent, an anti-fungal agent, and Loxasperse™ excipient base powder.

Disclosed herein is a capsule comprising a compounded composition, wherein the compounded composition comprises an anti-bacterial agent, an anti-fungal agent, and an excipient base powder comprising a blend of micronized xylitol and poloxamers.

In an aspect, the encapsulated compounded composition can be a dry powder formulation. In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the anti-fungal agent can be a dry powder. In an aspect, the anti-fungal agent can be an ointment. The anti-fungal agent can be pure or substantially pure. The anti-fungal agent can be obtained from a bulk source. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise from about 10% to about 40% w/w of the encapsulated compounded composition. In an aspect, the anti-bacterial agent can comprise from about 15% to about 35% w/w of the encapsulated compounded composition. In an aspect, the anti-bacterial agent can comprise from about 20% to about 30% w/w of the encapsulated compounded composition. In an aspect, the anti-bacterial agent can comprise about 25% w/w of the encapsulated compounded composition.

In an aspect, the anti-fungal agent can comprise from about 10% to about 40% w/w of the encapsulated compounded composition. In an aspect, the anti-fungal agent can comprise from about 15% to about 35% w/w of the encapsulated compounded composition. In an aspect, the anti-fungal agent can comprise from about 20% to about 30% w/w of the encapsulated compounded composition. In an aspect, the anti-fungal agent can comprise about 25% w/w of the encapsulated compounded composition.

In an aspect, the ratio of the anti-bacterial agent to the anti-fungal agent in the encapsulated compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1.25:1. See, e.g., Table 1.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect, the anti-bacterial agent of a disclosed encapsulated compounded composition can comprise mupirocin. In an aspect, the anti-bacterial agent of a disclosed encapsulated compounded composition can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect, a disclosed encapsulated compounded composition can comprise itraconazole. In an aspect, a disclosed encapsulated compounded composition can comprise fluconazole. In an aspect, a disclosed encapsulated compounded composition can comprise nystatin.

In an aspect, a disclosed encapsulated compounded composition can comprise mupirocin and itraconazole. In an aspect, a disclosed encapsulated compounded composition can comprise azithromycin and fluconazole. In an aspect, a disclosed encapsulated compounded composition can comprise mupirocin and nystatin.

In an aspect, a disclosed capsule can comprise about 100 mg to about 2000 mg of a compounded composition. For example, in an aspect, a disclosed capsule can comprise about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed compounded composition.

In an aspect, a disclosed encapsulated compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed encapsulated compounded composition can comprise one or more excipients or additives. In an aspect, excipients or additives include, but are not limited to, the following: solvents, surfactants, humectants, preservatives, flavorings, stabilizers (including antioxidants), binders, and colorants.

a. Mupirocin and/or Itraconazole

Disclosed herein is a capsule comprising a compounded composition, wherein the compounded composition comprises mupirocin and itraconazole. Disclosed herein is a capsule comprising a compounded composition comprising mupirocin, an anti-fungal agent, and an excipient base powder comprising a blend of micronized xylitol and poloxamers. Disclosed herein is a capsule comprising a compounded composition comprising an anti-bacterial agent, itraconazole, and an excipient base powder comprising a blend of micronized xylitol and poloxamers. Disclosed herein is a capsule comprising a compounded composition comprising mupirocin, itraconazole, and an excipient base powder comprising a blend of micronized xylitol and poloxamers. Disclosed herein is a capsule comprising a compounded composition comprising mupirocin, itraconazole, an excipient base powder comprising a blend of micronized xylitol and poloxamers, and at least one additional anti-infective agent. Disclosed herein is a capsule comprising a compounded composition comprising mupirocin, itraconazole, and Loxasperse™ excipient base powder.

b. Azithromycin and/or Fluconazole

Disclosed herein is a capsule comprising a compounded composition, wherein the compounded composition comprises azithromycin and fluconazole. Disclosed herein is a capsule comprising a compounded composition comprising azithromycin, an anti-fungal agent, and an excipient base powder comprising a blend of micronized xylitol and poloxamers. Disclosed herein is a capsule comprising a compounded composition comprising an anti-bacterial agent, fluconazole, and an excipient base powder comprising a blend of micronized xylitol and poloxamers. Disclosed herein is a capsule comprising a compounded composition comprising azithromycin, fluconazole, and an excipient base powder comprising a blend of micronized xylitol and poloxamers. Disclosed herein is a capsule comprising a compounded composition comprising azithromycin, fluconazole, an excipient base powder comprising a blend of micronized xylitol and poloxamers, and at least one additional anti-infective agent. Disclosed herein is a capsule comprising a compounded composition comprising azithromycin, fluconazole, and Loxasperse™ excipient base powder.

c. Mupirocin and/or Nystatin

Disclosed herein is a capsule comprising a compounded composition, wherein the compounded composition comprises mupirocin and nystatin. Disclosed herein is a capsule comprising a compounded composition comprising mupirocin, an anti-fungal agent, and an excipient base powder comprising a blend of micronized xylitol and poloxamers. Disclosed herein is a capsule comprising a compounded composition comprising an anti-bacterial agent, nystatin, and an excipient base powder comprising a blend of micronized xylitol and poloxamers. Disclosed herein is a capsule comprising a compounded composition comprising mupirocin, nystatin, and an excipient base powder comprising a blend of micronized xylitol and poloxamers. Disclosed herein is a capsule comprising a compounded composition comprising mupirocin, nystatin, an excipient base powder comprising a blend of micronized xylitol and poloxamers, and at least one additional anti-infective agent. Disclosed herein is a capsule comprising a compounded composition comprising mupirocin, nystatin, and Loxasperse™ excipient base powder.

1. Capsules Comprising an Anti-Bacterial Agent

Disclosed herein is a capsule comprising an anti-bacterial agent.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source.

In an aspect, a disclosed capsule can comprise an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect, a disclosed capsule can comprise mupirocin. In an aspect, a disclosed capsule can comprise azithromycin.

In an aspect, a disclosed capsule can comprise about 100 mg to about 2000 mg or a disclosed anti-bacterial agent. For example, in an aspect, a disclosed capsule can comprise about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed anti-bacterial agent.

For example, in an aspect, a disclosed capsule can comprise about 100 mg to about 1000 mg of mupirocin. In an aspect, a disclosed capsule can comprise about 100 mg of mupirocin, about 150 mg of mupirocin, about 200 mg of mupirocin, about 250 mg of mupirocin, about 300 mg of mupirocin, about 350 mg of mupirocin, about 400 mg of mupirocin, about 450 mg of mupirocin, about 500 mg of mupirocin, about 550 mg of mupirocin, about 600 mg of mupirocin, about 650 mg of mupirocin, about 700 mg of mupirocin, about 750 mg of mupirocin, about 800 mg of mupirocin, about 850 mg of mupirocin, about 900 mg of mupirocin, about 950 mg of mupirocin, or about 1000 mg of mupirocin, or more of mupirocin.

For example, in an aspect, a disclosed capsule can comprise about 100 mg to about 1000 mg of azithromycin. In an aspect, a disclosed capsule can comprise about 100 mg of azithromycin, about 150 mg of azithromycin, about 200 mg of azithromycin, about 250 mg of azithromycin, about 300 mg of azithromycin, about 350 mg of azithromycin, about 400 mg of azithromycin, about 450 mg of azithromycin, about 500 mg of azithromycin, about 550 mg of azithromycin, about 600 mg of azithromycin, about 650 mg of azithromycin, about 700 mg of azithromycin, about 750 mg of azithromycin, about 800 mg of azithromycin, about 850 mg of azithromycin, about 900 mg of azithromycin, about 950 mg of azithromycin, or about 1000 mg of azithromycin, or more of azithromycin. In an aspect, a disclosed capsule can comprise about 250 mg of azithromycin.

In an aspect, a disclosed capsule can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a capsule comprising mupirocin. Disclosed herein is a capsule comprising azithromycin.

2. Capsules Comprising an Anti-Fungal Agent

Disclosed herein is a capsule comprising an anti-fungal agent. In an aspect, the anti-fungal agent can be a dry powder. In an aspect, the anti-fungal agent can be an ointment. The anti-fungal agent can be pure or substantially pure. The anti-fungal agent can be obtained from a bulk source.

In an aspect, a disclosed capsule can comprise an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect, a disclosed capsule can comprise itraconazole. In an aspect, a disclosed capsule can comprise fluconazole. In an aspect, a disclosed capsule can comprise nystatin.

For example, in an aspect, a disclosed capsule can comprise about 100 mg to about 1000 mg of itraconazole. In an aspect, a disclosed capsule can comprise about 100 mg of itraconazole, about 150 mg of itraconazole, about 200 mg of itraconazole, about 250 mg of itraconazole, about 300 mg of itraconazole, about 350 mg of itraconazole, about 400 mg of itraconazole, about 450 mg of itraconazole, about 500 mg of itraconazole, about 550 mg of itraconazole, about 600 mg of itraconazole, about 650 mg of itraconazole, about 700 mg of itraconazole, about 750 mg of itraconazole, about 800 mg of itraconazole, about 850 mg of itraconazole, about 900 mg of itraconazole, about 950 mg of itraconazole, or about 1000 mg of itraconazole, or more of itraconazole.

For example, in an aspect, a disclosed capsule can comprise about 100 mg to about 1000 mg of fluconazole. In an aspect, a disclosed capsule can comprise about 100 mg of fluconazole, about 150 mg of fluconazole, about 200 mg of fluconazole, about 250 mg of fluconazole, about 300 mg of fluconazole, about 350 mg of fluconazole, about 400 mg of fluconazole, about 450 mg of fluconazole, about 500 mg of fluconazole, about 550 mg of fluconazole, about 600 mg of fluconazole, about 650 mg of fluconazole, about 700 mg of fluconazole, about 750 mg of fluconazole, about 800 mg of fluconazole, about 850 mg of fluconazole, about 900 mg of fluconazole, about 950 mg of fluconazole, or about 1000 mg of fluconazole, or more of fluconazole. In an aspect, a disclosed capsule can comprise about 200 mg of fluconazole.

For example, in an aspect, a disclosed capsule can comprise about 100 mg to about 1000 mg of nystatin. In an aspect, a disclosed capsule can comprise about 100 mg of nystatin, about 150 mg of nystatin, about 200 mg of nystatin, about 250 mg of nystatin, about 300 mg of nystatin, about 350 mg of nystatin, about 400 mg of nystatin, about 450 mg of nystatin, about 500 mg of nystatin, about 550 mg of nystatin, about 600 mg of nystatin, about 650 mg of nystatin, about 700 mg of nystatin, about 750 mg of nystatin, about 800 mg of nystatin, about 850 mg of fluconazole, about 900 mg of nystatin, about 950 mg of nystatin, or about 1000 mg of nystatin, or more of nystatin.

In an aspect, a disclosed capsule can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a capsule comprising itraconazole. Disclosed herein is a capsule comprising fluconazole. Disclosed herein is a capsule comprising nystatin.

B. Containers

1. Containers Comprising a Compounded Composition

Disclosed herein is a container comprising a disclosed compounded composition.

Disclosed herein is a container comprising a compounded composition, wherein the compounded composition can comprise an anti-bacterial agent, an anti-fungal agent, and an excipient base powder comprising a blend of micronized xylitol and poloxamers.

In an aspect, the container can be a glass container and can comprise a stopper or a seal. In an aspect, the container can be a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, the container can be a disposable packet. The disposable packet can be moisture free. In an aspect, the container can be a glass or non-glass vial.

In an aspect, a container can hold or accommodate about 5 mL, 10 mL, 15 mL, 25 mL, 50 mL, 75 mL, 100 mL, 125 mL, 150 mL, 175 mL, 200 mL, 250 mL, 300 mL, 350 mL, 400 mL, 450 mL, 500 mL, or 1000 mL of a liquid. In an aspect, a container can hold from about 25 mL to about 1000 mL.

In an aspect, a container can hold or accommodate about 5 g, 10 g, 15 g, 25 g, 50 g, 75 g, 100 g, 125 g, 150 g, 175 g, 200 g, 250 g, 300 g, 350 g, 400 g, 450 g, 500 g, or 1000 g of a compounded composition. In an aspect, a container can hold or accommodate about 15 g of a compounded composition. In an aspect, a container can hold or accommodate about 180 g of a compounded composition. In an aspect, a container can hold or accommodate about 450 g of a compounded composition. In an aspect, a container can hold or accommodate about 500 g of a compounded composition.

In an aspect, the compounded composition can be a dry powder formulation.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the anti-fungal agent can be a dry powder. In an aspect, the anti-fungal agent can be an ointment. The anti-fungal agent can be pure or substantially pure. The anti-fungal agent can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise from about 10% to about 40% w/w of the contained compounded composition. In an aspect, the anti-bacterial agent can comprise from about 15% to about 35% w/w of the contained compounded composition. In an aspect, the anti-bacterial agent can comprise from about 20% to about 30% w/w of the contained compounded composition. In an aspect, the anti-bacterial agent can comprise about 25% w/w of the contained compounded composition.

In an aspect, the anti-fungal agent can comprise from about 10% to about 40% w/w of the contained compounded composition. In an aspect, the anti-fungal agent can comprise from about 15% to about 35% w/w of the contained compounded composition. In an aspect, the anti-fungal agent can comprise from about 20% to about 30% w/w of the contained compounded composition. In an aspect, the anti-fungal agent can comprise about 25% w/w of the contained compounded composition.

In an aspect, the ratio of the anti-bacterial agent to the anti-fungal agent in the contained compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1.25:1. See, e.g., Table 1.

In an aspect, the anti-bacterial agent of the contained compounded composition can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect, the anti-bacterial agent of the contained compounded composition can comprise mupirocin. In an aspect, the anti-bacterial agent of the contained compounded composition can comprise azithromycin.

In an aspect, the anti-fungal agent of the contained compounded composition can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect, the anti-fungal agent of the contained compounded composition can comprise itraconazole. In an aspect, the anti-fungal agent of the contained compounded composition can comprise fluconazole. In an aspect, the anti-fungal agent of the contained compounded composition can comprise nystatin.

In an aspect, the contained compounded composition can comprise mupirocin and itraconazole. In an aspect, the contained compounded composition can comprise azithromycin and fluconazole. In an aspect, the contained compounded composition can comprise mupirocin and nystatin.

In an aspect, the contained compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a contained compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed container can comprise one or more capsules, each encapsulating a disclosed compounded composition.

Disclosed herein is a container comprising one or more capsules, each capsule comprising a compounded composition, wherein the compounded composition can comprise an anti-bacterial agent, an anti-fungal agent, and an excipient base powder comprising a blend of micronized xylitol and poloxamers.

a. Containers Comprising a Compounded Composition Comprising Mupirocin and/or Itraconazole Disclosed herein is a container comprising a compounded composition, wherein the compounded composition can comprise mupirocin, itraconazole, and an excipient base powder comprising a blend of micronized xylitol and poloxamers.

In an aspect, the container can be a glass container and can comprise a stopper or a seal. In an aspect, the container can be a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, the container can be a disposable packet. The disposable packet can be moisture free. In an aspect, the container can be a glass or non-glass vial.

In an aspect, a container can hold or accommodate about 5 mL, 10 mL, 15 mL, 25 mL, 50 mL, 75 mL, 100 mL, 125 mL, 150 mL, 175 mL, 200 mL, 250 mL, 300 mL, 350 mL, 400 mL, 450 mL, 500 mL, or 1000 mL of a liquid. In an aspect, a container can hold from about 25 mL to about 1000 mL.

In an aspect, a container can hold or accommodate about 5 g, 10 g, 15 g, 25 g, 50 g, 75 g, 100 g, 125 g, 150 g, 175 g, 200 g, 250 g, 300 g, 350 g, 400 g, 450 g, 500 g, or 1000 g of a compounded composition comprising mupirocin and itraconazole. In an aspect, a container can hold or accommodate about 15 g of a compounded composition. In an aspect, a container can hold or accommodate about 180 g of a compounded composition. In an aspect, a container can hold or accommodate about 450 g of a compounded composition. In an aspect, a container can hold or accommodate about 500 g of a compounded composition.

In an aspect, the compounded composition can be a dry powder formulation.

In an aspect, the mupirocin can be a dry powder. In an aspect, the mupirocin can be an ointment. The mupirocin can be pure or substantially pure. The mupirocin can be obtained from a bulk source. In an aspect, the itraconazole can be a dry powder. In an aspect, the itraconazole can be an ointment. The itraconazole can be pure or substantially pure. The itraconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the contained compounded composition. In an aspect, the mupirocin can comprise from about 15% to about 35% w/w of the contained compounded composition. In an aspect, the mupirocin can comprise from about 20% to about 30% w/w of the contained compounded composition. In an aspect, the mupirocin can comprise about 25% w/w of the contained compounded composition.

In an aspect, the itraconazole can comprise from about 10% to about 40% w/w of the contained compounded composition. In an aspect, the itraconazole can comprise from about 15% to about 35% w/w of the contained compounded composition. In an aspect, the itraconazole can comprise from about 20% to about 30% w/w of the contained compounded composition. In an aspect, the itraconazole can comprise about 25% w/w of the contained compounded composition.

In an aspect, the ratio of the mupirocin to the itraconazole in the contained compounded composition can be from about 1:4 to about 4:1. In an aspect, the ratio of the mupirocin to the itraconazole can be about 1:1. See, e.g., Table 2.

In an aspect, a contained compounded composition comprising mupirocin and itraconazole can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a contained compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition comprising mupirocin and itraconazole can be encapsulated in one or more capsules.

Disclosed herein is a container comprising a compounded composition, wherein the compounded composition can comprise an anti-bacterial agent, itraconazole, and an excipient base powder comprising a blend of micronized xylitol and poloxamers. Disclosed herein is a container comprising a compounded composition, wherein the compounded composition can comprise mupirocin, an anti-fungal agent, and an excipient base powder comprising a blend of micronized xylitol and poloxamers. Disclosed herein is a container comprising a compounded composition, wherein the compounded composition can comprise mupirocin, itraconazole, an excipient base powder comprising a blend of micronized xylitol and poloxamers, and at least one additional anti-infective agent. Disclosed herein is a container comprising one or more capsules, each capsule comprising a compounded composition, wherein the compounded composition can comprise mupirocin, itraconazole, and an excipient base powder comprising a blend of micronized xylitol and poloxamers.

b. Containers Comprising a Compounded Composition Comprising Azithromycin and/or Fluconazole Disclosed herein is a container comprising a compounded composition, wherein the compounded composition can comprise azithromycin, fluconazole, and an excipient base powder comprising a blend of micronized xylitol and poloxamers.

In an aspect, the container can be a glass container and can comprise a stopper or a seal. In an aspect, the container can be a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, the container can be a disposable packet. The disposable packet can be moisture free. In an aspect, the container can be a glass or non-glass vial.

In an aspect, a container can hold or accommodate about 5 mL, 10 mL, 15 mL, 25 mL, 50 mL, 75 mL, 100 mL, 125 mL, 150 mL, 175 mL, 200 mL, 250 mL, 300 mL, 350 mL, 400 mL, 450 mL, 500 mL, or 1000 mL of a liquid. In an aspect, a container can hold from about 25 mL to about 1000 mL.

In an aspect, a container can hold or accommodate about 5 g, 10 g, 15 g, 25 g, 50 g, 75 g, 100 g, 125 g, 150 g, 175 g, 200 g, 250 g, 300 g, 350 g, 400 g, 450 g, 500 g, or 1000 g of a compounded composition. In an aspect, a container can hold or accommodate about 15 g of a compounded composition. In an aspect, a container can hold or accommodate about 180 g of a compounded composition. In an aspect, a container can hold or accommodate about 450 g of a compounded composition.

In an aspect, the contained compounded composition can be a dry powder formulation. In an aspect, the azithromycin can be a dry powder. In an aspect, the azithromycin can be an ointment. The azithromycin can be pure or substantially pure. The azithromycin can be obtained from a bulk source. In an aspect, the fluconazole can be a dry powder. In an aspect, the fluconazole can be an ointment. The fluconazole can be pure or substantially pure. The fluconazole can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the fluconazole can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the azithromycin to the fluconazole in the contained compounded composition can be from about 1:4 to about 4:1. In an aspect, the ratio of the azithromycin to the fluconazole can be about 1:1. In an aspect, the ratio of the azithromycin to the fluconazole can be about 1.25:1. See, e.g., Table 3.

In an aspect, a contained compounded composition comprising azithromycin and fluconazole can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a contained compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a contained compounded composition comprising azithromycin and fluconazole can be encapsulated in one or more capsules.

Disclosed herein is a container comprising a compounded composition, wherein the compounded composition can comprise an anti-bacterial agent, fluconazole, and an excipient base powder comprising a blend of micronized xylitol and poloxamers.

Disclosed herein is a container comprising a compounded composition, wherein the compounded composition can comprise azithromycin, an anti-fungal agent, and an excipient base powder comprising a blend of micronized xylitol and poloxamers.

Disclosed herein is a container comprising a compounded composition, wherein the compounded composition can comprise azithromycin, fluconazole, an excipient base powder comprising a blend of micronized xylitol and poloxamers, and at least one additional anti-infective agent. Disclosed herein is a container comprising one or more capsules, each capsule comprising a compounded composition, wherein the compounded composition can comprise azithromycin, fluconazole, and an excipient base powder comprising a blend of micronized xylitol and poloxamers.

c. Containers Comprising a Compounded Composition Comprising Mupirocin and/or Nystatin Disclosed herein is a container comprising a compounded composition, wherein the compounded composition can comprise mupirocin, nystatin, and an excipient base powder comprising a blend of micronized xylitol and poloxamers.

In an aspect, the container can be a glass container and can comprise a stopper or a seal. In an aspect, the container can be a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, the container can be a disposable packet. The disposable packet can be moisture free. In an aspect, the container can be a glass or non-glass vial.

In an aspect, a container can hold or accommodate about 5 mL, 10 mL, 15 mL, 25 mL, 50 mL, 75 mL, 100 mL, 125 mL, 150 mL, 175 mL, 200 mL, 250 mL, 300 mL, 350 mL, 400 mL, 450 mL, 500 mL, or 1000 mL of a liquid. In an aspect, a container can hold from about 25 mL to about 1000 mL.

In an aspect, a container can hold or accommodate about 5 g, 10 g, 15 g, 25 g, 50 g, 75 g, 100 g, 125 g, 150 g, 175 g, 200 g, 250 g, 300 g, 350 g, 400 g, 450 g, 500 g, or 1000 g of a compounded composition. In an aspect, a container can hold or accommodate about 15 g of a compounded composition. In an aspect, a container can hold or accommodate about 180 g of a compounded composition. In an aspect, a container can hold or accommodate about 450 g of a compounded composition.

In an aspect, the contained compounded composition can be a dry powder formulation.

In an aspect, the mupirocin can be a dry powder. In an aspect, the mupirocin can be an ointment. In an aspect, the mupirocin can be a 2% ointment. The mupirocin can be pure or substantially pure. The mupirocin can be obtained from a bulk source. In an aspect, the nystatin can be a dry powder. In an aspect, the nystatin can be an ointment. The nystatin can be pure or substantially pure. The nystatin can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the contained compounded composition. In an aspect, the mupirocin can comprise from about 15% to about 35% w/w of the contained compounded composition. In an aspect, the mupirocin can comprise from about 20% to about 30% w/w of the contained compounded composition. In an aspect, the mupirocin can comprise about 25% w/w of the contained compounded composition.

In an aspect, the nystatin can comprise from about 10% to about 40% w/w of the contained compounded composition. In an aspect, the nystatin can comprise from about 15% to about 35% w/w of the contained compounded composition. In an aspect, the nystatin can comprise from about 20% to about 30% w/w of the contained compounded composition. In an aspect, the nystatin can comprise about 25% w/w of the contained compounded composition.

In an aspect, the ratio of the mupirocin to the nystatin in the contained compounded composition can be from about 1:4 to about 4:1. In an aspect, the ratio of the mupirocin to the nystatin can be about 1:1. In an aspect, the ratio of the mupirocin to the nystatin can be about 1.25:1. See, e.g., Table 3.

In an aspect, a contained compounded composition comprising azithromycin and fluconazole can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a contained compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a contained compounded composition comprising mupirocin and nystatin can be encapsulated in one or more capsules.

Disclosed herein is a container comprising a compounded composition, wherein the compounded composition can comprise an anti-bacterial agent, nystatin, and an excipient base powder comprising a blend of micronized xylitol and poloxamers. Disclosed herein is a container comprising a compounded composition, wherein the compounded composition can comprise mupirocin, an anti-fungal agent, and an excipient base powder comprising a blend of micronized xylitol and poloxamers. Disclosed herein is a container comprising a compounded composition, wherein the compounded composition can comprise mupirocin, nystatin, an excipient base powder comprising a blend of micronized xylitol and poloxamers, and at least one additional anti-infective agent. Disclosed herein is a container comprising one or more capsules, each capsule comprising a compounded composition, wherein the compounded composition can comprise mupirocin, nystatin, and an excipient base powder comprising a blend of micronized xylitol and poloxamers.

1. Containers Comprising an Anti-Bacterial Agent

Disclosed herein is a container comprising an anti-bacterial agent.

In an aspect, the contained anti-bacterial agent can be encapsulated in one or more capsules.

In an aspect, the container can be a glass container and can comprise a stopper or a seal. In an aspect, the container can be a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, the container can be a disposable packet. The disposable packet can be moisture free. In an aspect, the container can be a glass or non-glass vial.

In an aspect, a container can hold or accommodate about 5 mL, 10 mL, 15 mL, 25 mL, 50 mL, 75 mL, 100 mL, 125 mL, 150 mL, 175 mL, 200 mL, 250 mL, 300 mL, 350 mL, 400 mL, 450 mL, 500 mL, or 1000 mL of a liquid. In an aspect, a container can hold from about 25 mL to about 1000 mL.

In an aspect, a container can hold or accommodate about 5 g, 10 g, 15 g, 25 g, 50 g, 75 g, 100 g, 125 g, 150 g, 175 g, 200 g, 250 g, 300 g, 350 g, 400 g, 450 g, 500 g, or 1000 g of an anti-bacterial agent. In an aspect, a container can hold or accommodate about 15 g of an anti-bacterial agent. In an aspect, a container can hold or accommodate about 180 g of an anti-bacterial agent. In an aspect, a container can hold or accommodate about 450 g of an anti-bacterial agent. In an aspect, a container can hold or accommodate about 500 g of an anti-bacterial agent.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source.

In an aspect, the disclosed container can comprise an excipient base powder comprising a blend of micronized xylitol and poloxamers. In an aspect, the excipient base powder can comprise Loxasperse™ excipient base powder. The excipient base powder can comprise Loxasperse™ excipient base powder and XyliFos™ excipient base powder. In an aspect, an excipient base powder can be obtained from a bulk source.

In an aspect, the contained anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect, the contained anti-bacterial agent can comprise mupirocin. In an aspect, the contained anti-bacterial agent can comprise azithromycin.

In an aspect, a disclosed container can comprise one or more excipients or additives. In an aspect, excipients or additives include, but are not limited to, the following: solvents, surfactants, humectants, preservatives, flavorings, stabilizers (including antioxidants), binders, and colorants.

2. Containers Comprising an Anti-Fungal Agent

Disclosed herein is a container comprising an anti-fungal agent.

In an aspect, the contained anti-fungal agent can be encapsulated in one or more capsules.

In an aspect, the container can be a glass container and can comprise a stopper or a seal. In an aspect, the container can be a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, the container can be a disposable packet. The disposable packet can be moisture free. In an aspect, the container can be a glass or non-glass vial.

In an aspect, a container can hold or accommodate about 5 mL, 10 mL, 15 mL, 25 mL, 50 mL, 75 mL, 100 mL, 125 mL, 150 mL, 175 mL, 200 mL, 250 mL, 300 mL, 350 mL, 400 mL, 450 mL, 500 mL, or 1000 mL of a liquid. In an aspect, a container can hold from about 25 mL to about 1000 mL.

In an aspect, a container can hold or accommodate about 5 g, 10 g, 15 g, 25 g, 50 g, 75 g, 100 g, 125 g, 150 g, 175 g, 200 g, 250 g, 300 g, 350 g, 400 g, 450 g, 500 g, or 1000 g of an anti-fungal agent. In an aspect, a container can hold or accommodate about 15 g of an anti-fungal agent. In an aspect, a container can hold or accommodate about 180 g of an anti-fungal agent. In an aspect, a container can hold or accommodate about 450 g of an anti-fungal agent. In an aspect, a container can hold or accommodate about 500 g of an anti-fungal agent.

In an aspect, the anti-fungal agent can be a dry powder. In an aspect, the anti-fungal agent can be an ointment. In an aspect, the anti-fungal agent can be obtained from a bulk source. The anti-fungal agent can be pure or substantially pure.

In an aspect, the disclosed container can comprise an excipient base powder comprising a blend of micronized xylitol and poloxamers. In an aspect, the excipient base powder can comprise Loxasperse™ excipient base powder. The excipient base powder can comprise Loxasperse™ excipient base powder and XyliFos™ excipient base powder. In an aspect, an excipient base powder can be obtained from a bulk source.

In an aspect, the contained anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect, the contained anti-fungal agent can comprise itraconazole. In an aspect, the contained anti-fungal agent can comprise fluconazole. In an aspect, the contained anti-fungal agent can comprise nystatin.

In an aspect, a disclosed container comprising an anti-fungal agent can comprise one or more excipients or additives. In an aspect, excipients or additives include, but are not limited to, the following: solvents, surfactants, humectants, preservatives, flavorings, stabilizers (including antioxidants), binders, and colorants.

In an aspect, an anti-fungal agent can be encapsulated in one or more capsules.

B. Kits

1. Kits Comprising a Compounded Composition

Disclosed herein is a kit comprising a disclosed compounded composition.

Disclosed herein is a kit, comprising: one or more containers, each comprising a compounded composition, wherein the compounded composition can comprise a therapeutically effective amount of an anti-bacterial agent, a therapeutically effective amount of an anti-fungal agent, and an amount of an excipient base powder comprising a blend of micronized xylitol and poloxamers.

In an aspect, the kit can comprise instructions for using the compounded composition.

In an aspect, the kit can comprise a foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath. Heating agents and/or means to heat water in a compartment are known to the art.

In an aspect, the kit can comprise one or more funnels. In an aspect, the kit can comprise one or more mixing containers. In an aspect, the kit can comprise one or more scoops.

In an aspect, the kit can comprise a diluent for the compounded composition. In an aspect, the diluent can comprise sodium hypochlorite. In an aspect, the diluent can comprise Dakin's solution.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the anti-fungal agent can be a dry powder. In an aspect, the anti-fungal agent can be an ointment. The anti-fungal agent can be pure or substantially pure. The anti-fungal agent can be obtained from a bulk source.

In an aspect, the anti-bacterial agent can comprise from about 10% to about 40% w/w of the compounded composition. In an aspect, the anti-bacterial agent can comprise from about 15% to about 35% w/w of the compounded composition. In an aspect, the anti-bacterial agent can comprise from about 20% to about 30% w/w of the compounded composition. In an aspect, the anti-bacterial agent can comprise about 25% w/w of the compounded composition.

In an aspect, the anti-fungal agent can comprise from about 10% to about 40% w/w of the compounded composition. In an aspect, the anti-fungal agent can comprise from about 15% to about 35% w/w of the compounded composition. In an aspect, the anti-fungal agent can comprise from about 20% to about 30% w/w of the compounded composition. In an aspect, the anti-fungal agent can comprise about 25% w/w of the compounded composition.

In an aspect, the ratio of the anti-bacterial agent to the anti-fungal agent in the compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1:1.25. See, e.g., Table 1.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed kit, the compounded composition can comprise mupirocin.

In an aspect of a disclosed kit, the compounded composition can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed kit, the compounded composition can comprise itraconazole. In an aspect of a disclosed kit, the compounded composition can comprise fluconazole. In an aspect of a disclosed kit, the compounded composition can comprise nystatin.

In an aspect of a disclosed kit, the compounded composition can comprise mupirocin and itraconazole. In an aspect of a disclosed kit, the compounded composition can comprise azithromycin and fluconazole. In an aspect of a disclosed kit, the compounded composition can comprise mupirocin and nystatin.

In an aspect, a disclosed kit can comprise one or one or more containers of one or more additional anti-infective agents. In an aspect of a disclosed kit, a compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed kit can comprise a plurality of containers, each comprising a compounded composition comprising an anti-bacterial agent and an anti-fungal agent. In an aspect, a plurality can comprise about 30 containers, or about 60 containers, or about 90 containers, or more containers. In an aspect, a plurality can comprise 120 containers or more of the compounded composition. In an aspect, the kit can comprise an amount that the skilled person considers a monthly supply of the compounded composition.

Disclosed herein is a kit, comprising: one or more containers, each comprising a compounded composition, wherein the compounded composition can comprise a therapeutically effective amount of an anti-bacterial agent, a therapeutically effective amount of an anti-fungal agent, and an excipient base powder comprising a blend of micronized xylitol and poloxamers, and instructions for using the compounded composition.

In an aspect, the anti-bacterial agent can comprise mupirocin. In an aspect, the anti-fungal agent can comprise itraconazole. In an aspect of a disclosed kit, the compounded composition can comprise mupirocin and itraconazole. In an aspect, the anti-bacterial agent can comprise azithromycin. In an aspect, the anti-fungal agent can comprise fluconazole. In an aspect of a disclosed kit, the compounded composition can comprise azithromycin and fluconazole. In an aspect, the anti-bacterial agent can comprise mupirocin. In an aspect, the anti-fungal agent can comprise nystatin. In an aspect of a disclosed kit, the compounded composition can comprise mupirocin and nystatin.

Disclosed herein is a kit, comprising: one or more containers, each comprising a compounded composition, wherein the compounded composition can comprise a therapeutically effective amount of an anti-bacterial agent, a therapeutically effective amount of an anti-fungal agent, and an excipient base powder comprising a blend of micronized xylitol and poloxamers, a foot bath, and instructions for using the compounded composition.

In an aspect, the anti-bacterial agent can comprise mupirocin. In an aspect, the anti-fungal agent can comprise itraconazole. In an aspect of a disclosed kit, the compounded composition can comprise mupirocin and itraconazole. In an aspect, the anti-bacterial agent can comprise azithromycin. In an aspect, the anti-fungal agent can comprise fluconazole. In an aspect of a disclosed kit, the compounded composition can comprise azithromycin and fluconazole. In an aspect, the anti-bacterial agent can comprise mupirocin. In an aspect, the anti-fungal agent can comprise nystatin. In an aspect of a disclosed kit, the compounded composition can comprise mupirocin and nystatin.

a. Compounded Composition Comprising Mupirocin and/or Itraconazole

Disclosed herein is a kit, comprising: one or more containers, each comprising a compounded composition, wherein the compounded composition can comprise a therapeutically effective amount of mupirocin, a therapeutically effective amount of itraconazole, and an excipient base powder comprising a blend of micronized xylitol and poloxamers. Disclosed herein is a kit, comprising: one or more containers, each comprising a compounded composition, wherein the compounded composition can comprise a therapeutically effective amount of mupirocin, a therapeutically effective amount of itraconazole, and an excipient base powder comprising a blend of micronized xylitol and poloxamers, and instructions for using the compounded composition. Disclosed herein is a kit, comprising: one or more containers, each comprising a compounded composition, wherein the compounded composition can comprise a therapeutically effective amount of mupirocin, a therapeutically effective amount of itraconazole, and an excipient base powder comprising a blend of micronized xylitol and poloxamers, a foot bath, and instructions for using the compounded composition. In an aspect, a disclosed kit can comprise a plurality of containers, each comprising a compounded composition comprising mupirocin and itraconazole. In an aspect, a plurality can comprise about 30 containers, or about 60 containers, or about 90 containers, or more containers. In an aspect, a plurality can comprise 120 containers or more of the compounded composition comprising mupirocin and itraconazole. In an aspect, the kit can comprise an amount that the skilled person considers a monthly supply of the compounded composition.

b. Compounded Composition Comprising Azithromycin and/or Fluconazole

Disclosed herein is a kit, comprising: one or more containers, each comprising a compounded composition, wherein the compounded composition can comprise a therapeutically effective amount of azithromycin, a therapeutically effective amount of fluconazole, and an excipient base powder comprising a blend of micronized xylitol and poloxamers. Disclosed herein is a kit, comprising: one or more containers, each comprising a compounded composition, wherein the compounded composition can comprise a therapeutically effective amount of azithromycin, a therapeutically effective amount of fluconazole, and an excipient base powder comprising a blend of micronized xylitol and poloxamers, and instructions for using the compounded composition. Disclosed herein is a kit, comprising: one or more containers, each comprising a compounded composition, wherein the compounded composition can comprise a therapeutically effective amount of azithromycin, a therapeutically effective amount of fluconazole, and an excipient base powder comprising a blend of micronized xylitol and poloxamers, a foot bath, and instructions for using the compounded composition. In an aspect, the one or more containers, each comprising a compounded composition comprising azithromycin and fluconazole, can comprise about 30 containers, or about 60 containers, or about 90 containers, or more containers. In an aspect, a disclosed kit can comprise 120 containers or more of the compounded composition comprising azithromycin and fluconazole. In an aspect, the kit can comprise an amount that the skilled person considers a monthly supply of the compounded composition comprising azithromycin and fluconazole.

c. Compounded Composition Comprising Mupirocin and/or Nystatin

Disclosed herein is a kit, comprising: one or more containers, each comprising a compounded composition, wherein the compounded composition can comprise a therapeutically effective amount of mupirocin, a therapeutically effective amount of nystatin, and an excipient base powder comprising a blend of micronized xylitol and poloxamers. Disclosed herein is a kit, comprising: one or more containers, each comprising a compounded composition, wherein the compounded composition can comprise a therapeutically effective amount of mupirocin, a therapeutically effective amount of nystatin, and an excipient base powder comprising a blend of micronized xylitol and poloxamers, and instructions for using the compounded composition. Disclosed herein is a kit, comprising: one or more containers, each comprising a compounded composition, wherein the compounded composition can comprise a therapeutically effective amount of mupirocin, a therapeutically effective amount of nystatin, and an excipient base powder comprising a blend of micronized xylitol and poloxamers, a foot bath, and instructions for using the compounded composition. In an aspect, the one or more containers, each comprising a compounded composition comprising mupirocin and nystatin, can comprise about 30 containers, or about 60 containers, or about 90 containers, or more containers. In an aspect, a disclosed kit can comprise 120 containers or more of the compounded composition comprising mupirocin and nystatin. In an aspect, the kit can comprise an amount that the skilled person considers a monthly supply of the compounded composition comprising mupirocin and nystatin.

1. Kits Comprising an Anti-Bacterial Agent and an Anti-Fungal Agent

Disclosed herein is a kit comprising an anti-bacterial agent and an anti-fungal agent.

Disclosed herein is a kit, comprising: one or more containers comprising a therapeutically effective amount of an anti-bacterial agent and one or more containers comprising a therapeutically effective amount of an anti-fungal agent.

In an aspect, the kit can comprise instructions for using the anti-bacterial agent and the anti-fungal agent.

In an aspect, the kit can comprise a foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the anti-bacterial agent and the anti-fungal agent or both throughout the water contained within the foot bath. Heating agents and/or means to heat water in a compartment are known to the art.

In an aspect, the kit can comprise one or more funnels. In an aspect, the kit can comprise one or more mixing containers. In an aspect, the kit can comprise one or more scoops.

In an aspect, the kit can comprise a diluent for the anti-bacterial agent. In an aspect, the kit can comprise a diluent for the anti-fungal agent. In an aspect, the diluent can comprise sodium hypochlorite. In an aspect, the diluent can comprise Dakin's solution. In an aspect, the diluent for the anti-bacterial agent is the same as the diluent for the anti-fungal agent. In an aspect, the diluent for the anti-bacterial agent is different than the diluent for the anti-fungal agent.

In an aspect, a disclosed kit can comprise one or more containers comprising an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can be a dry powder. In an aspect, the anti-bacterial agent can be an ointment. The anti-bacterial agent can be pure or substantially pure. The anti-bacterial agent can be obtained from a bulk source. In an aspect, the anti-fungal agent can be a dry powder. In an aspect, the anti-fungal agent can be an ointment. The anti-fungal agent can be pure or substantially pure. The an anti-fungal agent can be obtained from a bulk source.

In an aspect, the amount of anti-bacterial agent used in a disclosed kit compared to the amount of anti-fungal agent used can be from about 1:4 to about 4:1. In an aspect, the amount of anti-bacterial agent used in a disclosed kit compared to the amount of anti-fungal agent used can be about 1:1. In an aspect, the amount of anti-bacterial agent used in a disclosed kit compared to the amount of anti-fungal agent used can be about 1.25:1.

In an aspect, the anti-bacterial agent in a disclosed kit can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed kit, the anti-bacterial agent can comprise mupirocin. In an aspect of a disclosed kit, the anti-bacterial agent can comprise azithromycin.

In an aspect, the anti-fungal agent of a disclosed kit can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed kit, the anti-fungal agent can comprise itraconazole. In an aspect of a disclosed kit, the anti-fungal agent can comprise fluconazole. In an aspect of a disclosed kit, the anti-fungal agent can comprise nystatin.

In an aspect, a disclosed kit can comprise mupirocin and itraconazole. In an aspect, a disclosed kit can comprise azithromycin and fluconazole. In an aspect, a disclosed kit can comprise mupirocin and nystatin.

In an aspect, a disclosed kit can comprise one or more containers, each comprising one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed kit can comprise a plurality of containers, each comprising an anti-bacterial agent. In an aspect, a plurality can comprise about 30 containers, or about 60 containers, or about 90 containers, or more containers. In an aspect, a plurality can comprise 120 containers or more of the anti-bacterial agent. In an aspect, the kit can comprise an amount that the skilled person considers a monthly supply of the anti-bacterial agent.

In an aspect, a disclosed kit can comprise a plurality of containers, each comprising an anti-fungal agent. In an aspect, a plurality can comprise about 30 containers, or about 60 containers, or about 90 containers, or more containers. In an aspect, a plurality can comprise 120 containers or more of the anti-fungal agent. In an aspect, the kit can comprise an amount that the skilled person considers a monthly supply of the anti-fungal agent.

Disclosed herein is a kit, comprising: one or more containers comprising a therapeutically effective amount of an anti-bacterial agent or one or more containers comprising a therapeutically effective amount of an anti-fungal agent, a foot bath, and instructions for using the anti-bacterial agent and the anti-fungal agent.

In an aspect, the anti-bacterial agent can comprise mupirocin. In an aspect, the anti-fungal agent can comprise itraconazole. In an aspect, a disclosed kit can comprise mupirocin and itraconazole. In an aspect, the anti-bacterial agent can comprise azithromycin. In an aspect, the anti-fungal agent can comprise fluconazole. In an aspect, a disclosed kit can comprise azithromycin and fluconazole. In an aspect, the anti-bacterial agent can comprise mupirocin. In an aspect, the anti-fungal agent can comprise nystatin. In an aspect, a disclosed kit can comprise mupirocin and nystatin.

Disclosed herein is a kit, comprising: one or more containers comprising a therapeutically effective amount of an anti-bacterial agent or one or more containers comprising a therapeutically effective amount of an anti-fungal agent, a foot bath, and instructions for using the anti-bacterial agent and the anti-fungal agent.

In an aspect, the anti-bacterial agent can comprise mupirocin. In an aspect, the anti-fungal agent can comprise itraconazole. In an aspect, a disclosed kit can comprise mupirocin and itraconazole. In an aspect, the anti-bacterial agent can comprise azithromycin. In an aspect, the anti-fungal agent can comprise fluconazole. In an aspect, a disclosed kit can comprise azithromycin and fluconazole. In an aspect, the anti-bacterial agent can comprise mupirocin. In an aspect, the anti-fungal agent can comprise nystatin. In an aspect, a disclosed kit can comprise mupirocin and nystatin.

a. Mupirocin and/or Itraconazole

Disclosed herein is a kit, comprising: one or more containers comprising a therapeutically effective amount of mupirocin and one or more containers comprising a therapeutically effective amount of itraconazole. Disclosed herein is a kit, comprising: one or more containers comprising a therapeutically effective amount of mupirocin and one or more containers comprising a therapeutically effective amount of itraconazole, and instructions for using the mupirocin and the itraconazole.

In an aspect, the kit can comprise a foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the mupirocin and the itraconazole or both throughout the water contained within the foot bath. Heating agents and/or means to heat water in a compartment are known to the art.

In an aspect, the kit can comprise one or more funnels. In an aspect, the kit can comprise one or more mixing containers. In an aspect, the kit can comprise one or more scoops.

In an aspect, the kit can comprise a diluent for the mupirocin. In an aspect, the kit can comprise a diluent for the itraconazole. In an aspect, the diluent can comprise sodium hypochlorite. In an aspect, the diluent can comprise Dakin's solution. In an aspect, the diluent for the mupirocin is the same as the diluent for the itraconazole. In an aspect, the diluent for the mupirocin is different than the diluent for the itraconazole.

In an aspect, a disclosed kit can comprise one or more containers comprising an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can be a dry powder. In an aspect, the mupirocin can be an ointment. The mupirocin can be pure or substantially pure. The mupirocin can be obtained from a bulk source. In an aspect, the itraconazole can be a dry powder. In an aspect, the itraconazole can be an ointment. The itraconazole can be pure or substantially pure. The itraconazole can be obtained from a bulk source.

In an aspect, the amount of the mupirocin used in a disclosed kit compared to the amount of the itraconazole used can be from about 1:4 to about 4:1. In an aspect, the amount of the mupirocin used in a disclosed kit compared to the amount of the itraconazole used can be about 1:1. In an aspect, the amount of the mupirocin used in a disclosed kit compared to the amount of the itraconazole used can be about 1.25:1.

In an aspect, a disclosed kit can comprise one or more containers comprising one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed kit can comprise a plurality containers of the mupirocin. For example, in an aspect, a disclosed kit can comprise about 30 containers of the mupirocin, or about 60 containers of the mupirocin, or about 90 containers of the mupirocin. In an aspect, a disclosed kit can comprise 120 containers of the mupirocin. In an aspect, the kit can comprise an amount that the skilled person considers a monthly supply of the mupirocin.

In an aspect, the kit can comprise a plurality of containers of the itraconazole. For example, in an aspect, a disclosed kit can comprise about 30 containers of the itraconazole, or about 60 containers of the itraconazole, or about 90 containers of the itraconazole. In an aspect, a disclosed kit can comprise 120 containers or more of the itraconazole. In an aspect, the kit can comprise an amount that the skilled person considers a monthly supply of the itraconazole.

Disclosed herein is a kit, comprising: one or more containers comprising a therapeutically effective amount of mupirocin, one or more containers comprising a therapeutically effective amount of itraconazole, a foot bath, and instructions for using the mupirocin and the itraconazole. Disclosed herein is a kit, comprising: one or more containers comprising a therapeutically effective amount of mupirocin, one or more containers comprising a therapeutically effective amount of itraconazole, a foot bath, one or more scoops, one or more mixing containers, a diluent, and instructions for using the mupirocin and the itraconazole.

b. Azithromycin and/or Fluconazole

Disclosed herein is a kit, comprising: one or more containers comprising a therapeutically effective amount of azithromycin and one or more containers comprising a therapeutically effective amount of fluconazole. Disclosed herein is a kit, comprising: one or more containers comprising a therapeutically effective amount of azithromycin, one or more containers comprising a therapeutically effective amount of fluconazole, and instructions for using the mupirocin and the itraconazole.

In an aspect, the kit can comprise a foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the azithromycin and the fluconazole or both throughout the water contained within the foot bath. Heating agents and/or means to heat water in a compartment are known to the art.

In an aspect, the kit can comprise one or more funnels. In an aspect, the kit can comprise one or more mixing containers. In an aspect, the kit can comprise one or more scoops.

In an aspect, the kit can comprise a diluent for the azithromycin. In an aspect, the kit can comprise a diluent for the fluconazole. In an aspect, the diluent can comprise sodium hypochlorite. In an aspect, the diluent can comprise Dakin's solution. In an aspect, the diluent for the azithromycin is the same as the diluent for the fluconazole. In an aspect, the diluent for the azithromycin is different than the diluent for the fluconazole.

In an aspect, a disclosed kit can comprise one or more containers comprising an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the azithromycin can be a dry powder. In an aspect, the azithromycin can be an ointment. The azithromycin can be pure or substantially pure. The azithromycin can be obtained from a bulk source. In an aspect, the fluconazole can be a dry powder. In an aspect, the fluconazole can be an ointment. The fluconazole can be pure or substantially pure. The fluconazole can be obtained from a bulk source.

In an aspect, the amount of the azithromycin used in a disclosed kit compared to the amount of the fluconazole used can be from about 1:4 to about 4:1. In an aspect, the amount of the azithromycin used in a disclosed kit compared to the amount of the fluconazole used can be about 1:1. In an aspect, the amount of the azithromycin used in a disclosed kit compared to the amount of the fluconazole used can be about 1.25:1.

In an aspect, a disclosed kit can comprise one or more containers comprising one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed kit can comprise a plurality containers of the azithromycin. For example, in an aspect, a disclosed kit can comprise about 30 containers of the azithromycin, or about 60 containers of the azithromycin, or about 90 containers of the azithromycin. In an aspect, a disclosed kit can comprise 120 containers of the azithromycin. In an aspect, the kit can comprise an amount that the skilled person considers a monthly supply of the azithromycin.

In an aspect, the kit can comprise a plurality of containers of the fluconazole. For example, in an aspect, a disclosed kit can comprise about 30 containers of the fluconazole, or about 60 containers of the fluconazole, or about 90 containers of the fluconazole. In an aspect, a disclosed kit can comprise 120 containers or more of the fluconazole. In an aspect, the kit can comprise an amount that the skilled person considers a monthly supply of the fluconazole.

Disclosed herein is a kit, comprising: one or more containers comprising a therapeutically effective amount of azithromycin, one or more containers comprising a therapeutically effective amount of fluconazole, a foot bath, and instructions for using the mupirocin and the itraconazole.

Disclosed herein is a kit, comprising: one or more containers, each comprising a therapeutically effective amount of azithromycin, one or more containers comprising a therapeutically effective amount of fluconazole, a foot bath, one or more scoops, one or more mixing containers, a diluent, and instructions for using the azithromycin and the fluconazole.

c. Mupirocin and/or Nystatin

Disclosed herein is a kit, comprising: one or more containers or tubes comprising a therapeutically effective amount of mupirocin and one or more containers comprising a therapeutically effective amount of nystatin. Disclosed herein is a kit, comprising: one or more containers or tubes comprising a therapeutically effective amount of mupirocin, one or more containers comprising a therapeutically effective amount of nystatin, and instructions for using the mupirocin and the nystatin.

In an aspect, the kit can comprise a foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the mupirocin and the nystatin or both throughout the water contained within the foot bath. Heating agents and/or means to heat water in a compartment are known to the art.

In an aspect, the kit can comprise one or more funnels. In an aspect, the kit can comprise one or more mixing containers. In an aspect, the kit can comprise one or more scoops. In an aspect, the kit can comprise one or more keys.

In an aspect, the kit can comprise a diluent for the mupirocin. In an aspect, the kit can comprise a diluent for the nystatin. In an aspect, the diluent can comprise sodium hypochlorite. In an aspect, the diluent can comprise Dakin's solution. In an aspect, the diluent for the mupirocin is the same as the diluent for the nystatin. In an aspect, the diluent for the mupirocin is different than the diluent for the nystatin.

In an aspect, a disclosed kit can comprise one or more containers comprising an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can be a dry powder. The mupirocin can be pure or substantially pure. In an aspect, the mupirocin can be obtained from a bulk source. In an aspect, the mupirocin can be an ointment. In an aspect, the mupirocin can be a 2% ointment. In an aspect, the mupirocin can be provided in a tube. For example, in an aspect, the mupirocin can be provided in a 22 gram tube. In an aspect, the nystatin can be a dry powder. In an aspect, the nystatin can be an ointment. The nystatin can be pure or substantially pure. In an aspect, the nystatin can be obtained from a bulk source. In an aspect, the nystatin can be provided in a container. For example, in an aspect, the nystatin can be provided in 15 gram container.

In an aspect, the kit can comprise a plurality of containers or tubes of mupirocin. For example, in an aspect, a disclosed kit can comprise about 30 containers or tubes of mupirocin, or about 60 containers or tubes of mupirocin, or about 90 containers or tubes of mupirocin. In an aspect, a disclosed kit can comprise 120 containers or tubes of mupirocin or more. In an aspect, the kit can comprise an amount that the skilled person considers a monthly supply of the mupirocin.

In an aspect, the kit can comprise a plurality of containers of nystatin. For example, in an aspect, a disclosed kit can comprise about 30 containers of nystatin, or about 60 containers of nystatin, or about 90 containers of nystatin. In an aspect, a disclosed kit can comprise 120 containers or more of nystatin. In an aspect, the kit can comprise an amount that the skilled person considers a monthly supply of the nystatin.

In an aspect, a disclosed kit can comprise one or more containers comprising one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

Disclosed herein is a kit, comprising: one or more containers or tubes comprising a therapeutically effective amount of mupirocin, one or more containers comprising a therapeutically effective amount of nystatin, a foot bath, and instructions for using the mupirocin and the nystatin. Disclosed herein is a kit, comprising: one or more containers or tubes comprising a therapeutically effective amount of mupirocin, one or more containers comprising a therapeutically effective amount of nystatin, a foot bath, one or more scoops, a mixing container, one or more keys, a diluent, and instructions for using the mupirocin, and the nystatin.

A. Methods of Making a Compounded Composition

Disclosed herein is a method of making a compounded composition comprising an anti-bacterial agent and an anti-fungal agent.

1. Compounded Composition Comprising an Anti-Bacterial Agent and an Anti-Fungal Agent Disclosed herein is a method of making a compounded composition, the method comprising: mixing a therapeutically effective amount of an anti-bacterial agent and a therapeutically effective amount of an anti-fungal agent with an excipient base powder comprising a blend of micronized xylitol and poloxamers to make a homogenous compounded composition.

In an aspect, the compounded composition can be a dry powder formulation.

In an aspect, the anti-bacterial agent can be a dry powder. In an aspect, the anti-bacterial agent can be an ointment. The anti-bacterial agent can be pure or substantially pure. In an aspect, the anti-fungal agent can be a dry powder. In an aspect, the anti-fungal agent can be an ointment. The anti-fungal agent can be pure or substantially pure.

In the method can comprise obtaining the anti-bacterial agent, the anti-fungal agent, the excipient base powder, or a combination thereof. In an aspect, obtaining the anti-bacterial agent, the anti-fungal agent, or the excipient base powder can comprise obtaining a bulk source of the anti-bacterial agent, a bulk source of the anti-fungal agent, a bulk source of the excipient base powder, or a combination thereof.

In an aspect, the excipient base powder can comprise Loxasperse™ excipient base powder. In an aspect, the excipient base powder can comprise Loxasperse™ excipient base powder and XyliFos™ excipient base powder.

In an aspect, the anti-bacterial agent can comprise from about 10% to about 40% w/w of the compounded composition. In an aspect, the anti-bacterial agent can comprise from about 15% to about 35% w/w of the compounded composition. In an aspect, the anti-bacterial agent can comprise from about 20% to about 30% w/w of the compounded composition. In an aspect, the anti-bacterial agent can comprise about 25% w/w of the compounded composition.

In an aspect, the anti-fungal agent can comprise from about 10% to about 40% w/w of the compounded composition. In an aspect, the anti-fungal agent can comprise from about 15% to about 35% w/w of the compounded composition. In an aspect, the anti-fungal agent can comprise from about 20% to about 30% w/w of the compounded composition. In an aspect, the anti-fungal agent can comprise about 25% w/w of the compounded composition.

In an aspect, the ratio of the anti-bacterial agent to the anti-fungal agent in the compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1.25:1. See, e.g., Table 2.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed method, the anti-bacterial agent can comprise mupirocin. In an aspect of a disclosed method, the anti-bacterial agent can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed method, the anti-fungal agent can comprise itraconazole. In an aspect of a disclosed method, the anti-fungal agent can comprise fluconazole. In an aspect of a disclosed method, the anti-fungal agent can comprise nystatin.

In an aspect of a disclosed method, the anti-bacterial agent can comprise mupirocin and the anti-fungal agent can comprise itraconazole. In an aspect of a disclosed method, the anti-bacterial agent can comprise azithromycin and the anti-fungal agent can comprise fluconazole. In an aspect of a disclosed method, the anti-bacterial agent can comprise mupirocin and the anti-fungal agent can comprise nystatin.

In an aspect, the method can comprise mixing a therapeutically effective amount of an additional anti-infective agent with the compounded composition. In an aspect, the additional anti-infective agent can be a dry powder. In an aspect, the additional anti-infective agent can be an ointment. The additional anti-infective can be pure or substantially pure. The additional anti-infective agent can be obtained from a bulk source.

In an aspect, additional the anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra. In an aspect, the method can comprise obtaining the additional anti-infective agent. In an aspect, obtaining the additional anti-infective agent can comprise obtaining a bulk source of the anti-infective agent.

In an aspect, the method can comprise packaging the compounded composition into a container and sealing the container. In an aspect, the method can comprise sterilizing the container comprising the compounded composition.

2. Compounded Composition Comprising Mupirocin and/or Itraconazole

Disclosed herein is a method of making a compounded composition, the method comprising: mixing a therapeutically effective amount of mupirocin and a therapeutically effective amount of itraconazole with an excipient base powder comprising a blend of micronized xylitol and poloxamers to make a homogenous compounded composition.

In an aspect, the compounded composition can be a dry powder formulation.

In an aspect, the mupirocin can be a dry powder. In an aspect, the mupirocin can be an ointment. The mupirocin can be pure or substantially pure. In an aspect, the itraconazole can be a dry powder. In an aspect, the itraconazole can be an ointment. The itraconazole can be pure or substantially pure.

In an aspect, the method can comprise obtaining the mupirocin, the itraconazole, the excipient base powder, or a combination thereof. In an aspect, obtaining the mupirocin, the itraconazole, or the excipient base powder can comprise obtaining a bulk source of the mupirocin, a bulk source of the itraconazole, a bulk source of the excipient base powder, or obtaining a combination thereof.

In an aspect, the excipient base powder can comprise Loxasperse™ excipient base powder. In an aspect, the excipient base powder can comprise Loxasperse™ excipient base powder and XyliFos™ excipient base powder.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the itraconazole can comprise from about 10% to about 40% w/w of the compounded composition. In an aspect, the itraconazole can comprise from about 15% to about 35% w/w of the compounded composition. In an aspect, the itraconazole can comprise from about 20% to about 30% w/w of the compounded composition. In an aspect, the itraconazole can comprise about 25% w/w of the compounded composition.

In an aspect, the ratio of the mupirocin to the itraconazole in the compounded composition can be from about 1:4 to about 4:1. In an aspect, the ratio of the mupirocin to the itraconazole can be about 1:1. In an aspect, the ratio of the mupirocin to the itraconazole can be about 1.25:1. See, e.g., Table 2.

In an aspect, the method can comprise mixing a therapeutically effective amount of an additional anti-infective agent with the compounded composition.

In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra. In an aspect, the method can comprise obtaining the additional anti-infective agent. In an aspect, obtaining the additional anti-infective agent can comprise obtaining a bulk source of the anti-infective agent.

In an aspect, the method can comprise packaging the compounded composition into a container and sealing the container. In an aspect, the method can comprise sterilizing the container comprising the compounded composition comprising mupirocin and itraconazole.

Disclosed herein is a method of making a compounded composition, the method comprising: mixing a therapeutically effective amount of mupirocin and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of an anti-bacterial agent and a therapeutically effective amount of itraconazole with an excipient base powder comprising a blend of micronized xylitol and poloxamers to make a homogenous compounded composition.

3. Compounded Composition Comprising Azithromycin and/or Fluconazole

Disclosed herein is a method of making a compounded composition, the method comprising: mixing a therapeutically effective amount of azithromycin and a therapeutically effective amount of fluconazole with an excipient base powder comprising a blend of micronized xylitol and poloxamers to make a homogenous compounded composition.

In an aspect, the compounded composition can be a dry powder formulation. In an aspect, the azithromycin can be a dry powder. In an aspect, the azithromycin can be an ointment. The azithromycin can be pure or substantially pure. In an aspect, the fluconazole can be a dry powder. In an aspect, the fluconazole can be an ointment. The fluconazole can be pure or substantially pure.

In an aspect, the method can comprise obtaining the azithromycin, the fluconazole, the excipient base powder, or a combination thereof. In an aspect, obtaining the azithromycin, the fluconazole, or the excipient base powder can comprise obtaining a bulk source of the azithromycin, a bulk source of the fluconazole, a bulk source of the excipient base powder, or obtaining a combination thereof.

In an aspect, the excipient base powder can comprise Loxasperse™ excipient base powder. In an aspect, the excipient base powder can comprise Loxasperse™ excipient base powder and XyliFos™ excipient base powder.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the fluconazole can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the azithromycin to the fluconazole in the compounded composition can be from about 1:4 to about 4:1. In an aspect, the ratio of the azithromycin to the fluconazole can be about 1:1. In an aspect, the ratio of the azithromycin to the fluconazole can be about 1.25:1. See, e.g., Table 3.

In an aspect, the method can comprise mixing a therapeutically effective amount of an additional anti-infective agent with the compounded composition. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source.

In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra. In an aspect, the method can comprise obtaining the additional anti-infective agent. In an aspect, obtaining the additional anti-infective agent can comprise obtaining a bulk source of the anti-infective agent.

In an aspect, the method can comprise packaging the compounded composition into a container and sealing the container. In an aspect, the method can comprise sterilizing the container comprising the compounded composition comprising azithromycin and fluconazole.

Disclosed herein is a method of making a compounded composition, the method comprising: mixing a therapeutically effective amount of azithromycin and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of an anti-bacterial agent and a therapeutically effective amount of fluconazole with an excipient base powder comprising a blend of micronized xylitol and poloxamers to make a homogenous compounded composition.

Disclosed herein is a method of making a compounded composition, the method comprising: mixing a therapeutically effective amount of azithromycin and a therapeutically effective amount of fluconazole with an excipient base powder comprising a blend of micronized xylitol and poloxamers to make a homogenous compounded composition, and encapsulating the homogenous compounded composition in one or more capsules.

4. Compounded Composition Comprising Mupirocin and/or Nystatin

Disclosed herein is a method of making a compounded composition, the method comprising: mixing a therapeutically effective amount of mupirocin and a therapeutically effective amount of nystatin with an excipient base powder comprising a blend of micronized xylitol and poloxamers to make a homogenous compounded composition.

In an aspect, the compounded composition can be a dry powder formulation.

In an aspect, the mupirocin can be a dry powder. The mupirocin can be pure or substantially pure. In an aspect, the mupirocin can be an ointment. In an aspect, the mupirocin can be a 2% ointment. In an aspect, the nystatin can be a dry powder. In an aspect, the nystatin can be an ointment. The nystatin can be pure or substantially pure.

In an aspect, the method can comprise obtaining the mupirocin, the nystatin, the excipient base powder, or a combination thereof. In an aspect, obtaining the mupirocin, the nystatin, or the excipient base powder can comprise obtaining a bulk source of the mupirocin, a bulk source of the nystatin, a bulk source of the excipient base powder, or obtaining a combination thereof.

In an aspect, the excipient base powder can comprise Loxasperse™ excipient base powder. In an aspect, the excipient base powder can comprise Loxasperse™ excipient base powder and XyliFos™ excipient base powder.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the nystatin can comprise from about 10% to about 40% w/w of the compounded composition. In an aspect, the nystatin can comprise from about 15% to about 35% w/w of the compounded composition. In an aspect, the nystatin can comprise from about 20% to about 30% w/w of the compounded composition. In an aspect, the nystatin can comprise about 25% w/w of the compounded composition.

In an aspect, the ratio of the mupirocin to the nystatin in the compounded composition can be from about 1:4 to about 4:1. In an aspect, the ratio of the mupirocin the nystatin can be about 1:1. In an aspect, the ratio of the mupirocin to nystatin can be about 1.25:1.

In an aspect, the method can comprise mixing a therapeutically effective amount of an additional anti-infective agent with the compounded composition. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source.

In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra. In an aspect, the method can comprise obtaining the additional anti-infective agent. In an aspect, obtaining the additional anti-infective agent can comprise obtaining a bulk source of the anti-infective agent.

In an aspect, the method can comprise packaging the compounded composition into a container and sealing the container. In an aspect, the method can comprise sterilizing the container comprising the compounded composition comprising mupirocin and nystatin.

Disclosed herein is a method of making a compounded composition, the method comprising: mixing a therapeutically effective amount of mupirocin and a therapeutically effective amount of an anti-fungal agent with an excipient base powder comprising a blend of micronized xylitol and poloxamers to make a homogenous compounded composition.

Disclosed herein is a method of making a compounded composition, the method comprising: mixing a therapeutically effective amount of an anti-bacterial agent and a therapeutically effective amount of nystatin with an excipient base powder comprising a blend of micronized xylitol and poloxamers to make a homogenous compounded composition.

B. Methods of Treating of Preventing an Infection Using a Compounded Composition Disclosed herein is a method of treating or preventing an infection, the method comprising: (i) adding a compounded composition to water contained within a foot bath; (ii) agitating the water contained within the foot bath; and (iii) contacting the agitated water with at least a part of one or both feet of a subject. Disclosed herein is a method of treating or preventing an infection, the method comprising: (i) mixing a compounded composition with a diluent to create a solution; (ii) adding the solution to water contained within a foot bath; (iii) agitating the water contained within the foot bath; and (iv) contacting the agitated water with at least part of one or both feet of a subject.

1. Compounded Composition Comprising an Anti-Bacterial Agent and an Anti-Fungal Agent Disclosed herein is a method of treating or preventing an infection, the method comprising: (i) adding a compounded composition comprising an anti-bacterial agent and an anti-fungal agent to water contained within a foot bath; (ii) agitating the water contained within the foot bath; and (iii) contacting the agitated water with at least a part of one or both feet of a subject.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iii) daily. In an aspect, the method can comprise repeating steps (i)-(iii) daily until the bacterial infection or suspected bacterial infection can be eradicated. In an aspect, the method can comprise repeating steps (i)-(iii) daily until the fungal infection or suspected fungal infection can be eradicated. In an aspect, the method can comprise repeating steps (i)-(iii) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath. Heating agents and/or means to heat water in a compartment are known to the art.

In an aspect, the compounded composition can comprise an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the compounded composition can be a dry powder formulation. In an aspect, the anti-bacterial agent can be obtained from a bulk source. The anti-bacterial agent can be pure or substantially pure. In an aspect, the anti-fungal agent can be obtained from a bulk source. The anti-fungal agent can be pure or substantially pure.

In an aspect, the anti-bacterial agent can comprise from about 10% to about 40% w/w of the compounded composition. In an aspect, the anti-bacterial agent can comprise from about 15% to about 35% w/w of the compounded composition. In an aspect, the anti-bacterial agent can comprise from about 20% to about 30% w/w of the compounded composition. In an aspect, the anti-bacterial agent can comprise about 25% w/w of the compounded composition.

In an aspect, the anti-fungal agent can comprise from about 10% to about 40% w/w of the compounded composition. In an aspect, the anti-fungal agent can comprise from about 15% to about 35% w/w of the compounded composition. In an aspect, the anti-fungal agent can comprise from about 20% to about 30% w/w of the compounded composition. In an aspect, the anti-fungal agent can comprise about 25% w/w of the compounded composition.

In an aspect, the ratio of the anti-bacterial agent to the anti-fungal agent in the compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1.25:1. See, e.g., Table 1.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed method, the anti-bacterial agent can comprise mupirocin. In an aspect of a disclosed method, the anti-bacterial agent can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed method, the anti-fungal agent can comprise itraconazole. In an aspect of a disclosed method, the anti-fungal agent can comprise fluconazole. In an aspect of a disclosed method, the a the anti-fungal agent can comprise nystatin.

In an aspect of a disclosed method, the anti-bacterial agent can comprise mupirocin and the anti-fungal agent can comprise itraconazole. In an aspect of a disclosed method, the anti-bacterial agent can comprise azithromycin and the anti-fungal agent can comprise fluconazole. In an aspect of a disclosed method, the anti-bacterial agent can comprise mupirocin and the anti-fungal agent can comprise nystatin.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. In an aspect, the method can comprise orally administering to the subject a pharmaceutical composition comprising an anti-fungal agent. In an aspect, the method can comprise orally administering to the subject a pharmaceutical composition comprising an anti-bacterial agent and a pharmaceutical composition comprising an anti-fungal agent. In an aspect, the method can comprise orally administering to the subject a pharmaceutical composition comprising an anti-bacterial agent and a pharmaceutical composition comprising an anti-fungal agent.

In an aspect, a disclosed compounded composition comprising an anti-bacterial agent and an anti-fungal agent can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein is a method of treating or preventing an infection, the method comprising: (i) mixing a compounded composition comprising an anti-bacterial agent and an anti-fungal agent with a diluent to create a solution; (ii) adding the solution to water contained within a foot bath; (iii) agitating the water contained within the foot bath; and (iv) contacting the agitated water with at least part of one or both feet of a subject.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the compounded composition and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the compounded composition can be a dry powder formulation. In an aspect, the anti-bacterial agent can be obtained from a bulk source. The anti-bacterial agent can be pure or substantially pure. In an aspect, the anti-fungal agent can be obtained from a bulk source. The anti-fungal agent can be pure or substantially pure.

In an aspect, the compounded composition can comprise and excipient base powder. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the anti-bacterial agent can comprise from about 10% to about 40% w/w of the compounded composition. In an aspect, the anti-bacterial agent can comprise from about 15% to about 35% w/w of the compounded composition. In an aspect, the anti-bacterial agent can comprise from about 20% to about 30% w/w of the compounded composition. In an aspect, the anti-bacterial agent can comprise about 25% w/w of the compounded composition.

In an aspect, the anti-fungal agent can comprise from about 10% to about 40% w/w of the compounded composition. In an aspect, the anti-fungal agent can comprise from about 15% to about 35% w/w of the compounded composition. In an aspect, the anti-fungal agent can comprise from about 20% to about 30% w/w of the compounded composition. In an aspect, the anti-fungal agent can comprise about 25% w/w of the compounded composition.

In an aspect, the ratio of the anti-bacterial agent to the anti-fungal agent in the compounded composition can be from about 1:4 to about 4:1. In an aspect, the ratio of the anti-bacterial agent to the anti-fungal agent can be about 1:1. In an aspect, the ratio of the anti-bacterial agent to the anti-fungal agent can be about 1.25:1. See, e.g., Table 1.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed method, the anti-bacterial agent can comprise mupirocin.

In an aspect of a disclosed method, the anti-bacterial agent can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed method, the anti-fungal agent can comprise itraconazole. In an aspect of a disclosed method, the anti-fungal agent can comprise fluconazole. In an aspect of a disclosed method, the anti-fungal agent can comprise nystatin.

In an aspect of a disclosed method, the anti-bacterial agent can comprise mupirocin and the anti-fungal agent can comprise itraconazole. In an aspect of a disclosed method, the anti-bacterial agent can comprise azithromycin and the anti-fungal agent can comprise fluconazole. In an aspect of a disclosed method, the anti-bacterial agent can comprise mupirocin and the anti-fungal agent can comprise nystatin.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. In an aspect, the method can comprise orally administering to the subject a pharmaceutical composition comprising an anti-fungal agent. In an apsect, the method can comprise orally administering to the subject a pharmaceutical composition comprising an anti-bacterial agent and a pharmaceutical composition comprising an anti-fungal agent.

In an aspect, a disclosed compounded composition comprising an anti-bacterial agent and an anti-fungal agent can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

2. Compounded Composition Comprising Mupirocin and/or Itraconazole

Disclosed herein is a method of treating or preventing an infection, the method comprising: (i) adding a compounded composition comprising mupirocin and itraconazole to water contained within a foot bath; (ii) agitating the water contained within the foot bath; and (iii) contacting the agitated water with at least a part of one or both feet of a subject.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iii) daily. In an aspect, the method can comprise repeating steps (i)-(iii) daily until the bacterial infection or suspected bacterial infection can be eradicated. In an aspect, the method can comprise repeating steps (i)-(iii) daily until the fungal infection or suspected fungal infection can be eradicated. In an aspect, the method can comprise repeating steps (i)-(iii) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath. Heating agents and/or means to heat water in a compartment are known to the art.

In an aspect, the compounded composition can comprise an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the compounded composition can be a dry powder formulation.

In an aspect, the mupirocin can be a dry powder. In an aspect, the mupirocin can be an ointment. The anti-bacterial agent can be pure or substantially pure. In an aspect, the mupirocin can be obtained from a bulk source. In an aspect, the itraconazole can be a dry powder. In an aspect, the itraconazole can be an ointment. The itraconazole can be pure or substantially pure. In an aspect, the itraconazole can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the itraconazole can comprise from about 10% to about 40% w/w of the compounded composition. In an aspect, the itraconazole can comprise from about 15% to about 35% w/w of the compounded composition. In an aspect, the itraconazole can comprise from about 20% to about 30% w/w of the compounded composition. In an aspect, the itraconazole can comprise about 25% w/w of the compounded composition.

In an aspect, the ratio of the mupirocin to the itraconazole in the compounded composition can be from about 1:4 to about 4:1. In an aspect, the ratio of the mupirocin to the itraconazole can be about 1:1. In an aspect, the ratio of the mupirocin to the itraconazole can be about 1.25:1. See, e.g., Table 1.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an apsect, the method can comprise orally administering to the subject a pharmaceutical composition comprising an anti-bacterial agent and a pharmaceutical composition comprising an anti-fungal agent.

In an aspect, a disclosed compounded composition comprising mupirocin and itraconazole can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein is a method of treating or preventing an infection, the method comprising: (i) mixing a compounded composition comprising mupirocin and itraconazole with a diluent to create a solution; (ii) adding the solution to water contained within a foot bath; (iii) agitating the water contained within the foot bath; and (iv) contacting the agitated water with at least part of one or both feet of a subject.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the compounded composition and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the compounded composition can comprise an excipient base powder comprising a blend of micronized xylitol and poloxamers. In an aspect, the compounded composition can be a dry powder formulation. In an aspect, the mupirocin can be obtained from a bulk source. The mupirocin can be pure or substantially pure. In an aspect, the itraconazole can be obtained from a bulk source. The itraconazole can be pure or substantially pure.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the itraconazole can comprise from about 10% to about 40% w/w of the compounded composition. In an aspect, the itraconazole can comprise from about 15% to about 35% w/w of the compounded composition. In an aspect, the itraconazole can comprise from about 20% to about 30% w/w of the compounded composition. In an aspect, the itraconazole can comprise about 25% w/w of the compounded composition.

In an aspect, the ratio of the mupirocin to the itraconazole in the compounded composition can be from about 1:4 to about 4:1. In an aspect, the ratio of the mupirocin to the itraconazole can be about 1:1. See, e.g., Table 1.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source.

In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an apsect, the method can comprise orally administering to the subject a pharmaceutical composition comprising an anti-bacterial agent and a pharmaceutical composition comprising an anti-fungal agent.

In an aspect, a disclosed compounded composition comprising mupirocin and itraconazole can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

3. Compounded Composition Comprising Azithromycin and/or Fluconazole

Disclosed herein is a method of treating or preventing an infection, the method comprising: (i) adding a compounded composition comprising azithromycin and fluconazole to water contained within a foot bath; (ii) agitating the water contained within the foot bath; and (iii) contacting the agitated water with at least a part of one or both feet of a subject.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iii) daily. In an aspect, the method can comprise repeating steps (i)-(iii) daily until the bacterial infection or suspected bacterial infection can be eradicated. In an aspect, the method can comprise repeating steps (i)-(iii) daily until the fungal infection or suspected fungal infection can be eradicated. In an aspect, the method can comprise repeating steps (i)-(iii) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath. Heating agents and/or means to heat water in a compartment are known to the art.

In an aspect, the compounded composition can comprise an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the compounded composition can be a dry powder formulation. In an aspect, the azithromycin can be obtained from a bulk source. The azithromycin can be pure or substantially pure. In an aspect, the fluconazole can be obtained from a bulk source. The fluconazole can be pure or substantially pure.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the fluconazole can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the azithromycin to the fluconazole in the compounded composition can be from about 1:4 to about 4:1. In an aspect, the ratio of azithromycin to the fluconazole can be about 1:1. In an aspect, the ratio of the azithromycin to the fluconazole be about 1.25:1. See, e.g., Table 3.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an apsect, the method can comprise orally administering to the subject a pharmaceutical composition comprising an anti-bacterial agent and a pharmaceutical composition comprising an anti-fungal agent.

In an aspect, a disclosed compounded composition comprising azithromycin and fluconazole can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein is a method of treating or preventing an infection, the method comprising: (i) mixing a compounded composition comprising azithromycin and fluconazole with a diluent to create a solution; (ii) adding the solution to water contained within a foot bath; (iii) agitating the water contained within the foot bath; and (iv) contacting the agitated water with at least part of one or both feet of a subject.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the compounded composition and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the compounded composition can comprise an excipient base powder comprising a blend of micronized xylitol and poloxamers. In an aspect, the compounded composition can be a dry powder formulation. In an aspect, the azithromycin can be obtained from a bulk source. The azithromycin can be pure or substantially pure. In an aspect, the fluconazole can be obtained from a bulk source. The fluconazole can be pure or substantially pure.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the azithromycin can comprise from about 10% to about 60% w/w of the compounded composition. In an aspect, the azithromycin can comprise from about 20% to about 50% w/w of the compounded composition. In an aspect, the azithromycin can comprise from about 30% to about 40% w/w of the compounded composition. In an aspect, the azithromycin can comprise about 25% w/w of the compounded composition. In an aspect, the azithromycin can comprise about 50% w/w of the compounded composition.

In an aspect, the fluconazole can comprise from about 10% to about 60% w/w of the compounded composition. In an aspect, the fluconazole can comprise from about 20% to about 50% w/w of the compounded composition. In an aspect, the fluconazole can comprise from about 30% to about 40% w/w of the compounded composition. In an aspect, the fluconazole can comprise about 25% w/w of the compounded composition. In an aspect, the fluconazole can comprise about 50% w/w of the compounded composition.

In an aspect, the ratio of the azithromycin to the fluconazole in the compounded composition can be from about 1:4 to about 4:1. In an aspect, the ratio of the azithromycin to the fluconazole can be about 1:1. In an aspect, the ratio of the azithromycin to the fluconazole can be about 1.25:1. See, e.g., Table 1.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, a disclosed compounded composition comprising azithromycin and fluconazole can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

4. Compounded Composition Comprising Mupirocin and/or Nystatin

Disclosed herein is a method of treating or preventing an infection, the method comprising: (i) adding a compounded composition comprising mupirocin and nystatin to water contained within a foot bath; (ii) agitating the water contained within the foot bath; and (iii) contacting the agitated water with at least a part of one or both feet of a subject.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iii) daily. In an aspect, the method can comprise repeating steps (i)-(iii) daily until the bacterial infection or suspected bacterial infection can be eradicated. In an aspect, the method can comprise repeating steps (i)-(iii) daily until the fungal infection or suspected fungal infection can be eradicated. In an aspect, the method can comprise repeating steps (i)-(iii) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath. Heating agents and/or means to heat water in a compartment are known to the art.

In an aspect, the compounded composition can comprise an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the compounded composition can be a dry powder formulation.

In an aspect, the mupirocin can be a dry powder. In an aspect, the mupirocin can be an ointment. In an aspect, the mupirocin can be a 2% ointment. The mupirocin can be pure or substantially pure. The mupirocin can be obtained from a bulk source. In an aspect, the nystatin can be a dry powder. In an aspect, the nystatin can be an ointment. The nystatin can be pure or substantially pure. The nystatin can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the nystatin can comprise from about 10% to about 40% w/w of the compounded composition. In an aspect, the nystatin can comprise from about 15% to about 35% w/w of the compounded composition. In an aspect, the nystatin can comprise from about 20% to about 30% w/w of the compounded composition. In an aspect, the nystatin can comprise about 25% w/w of the compounded composition.

In an aspect, the ratio of the mupirocin to the nystatin in the compounded composition can be from about 1:4 to about 4:1. In an aspect, the ratio of the mupirocin to the nystatin can be about 1:1. In an aspect, the ratio of the mupirocin to the nystatin can be about 1.25:1. See, e.g., Table 3.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, a disclosed compounded composition comprising mupirocin and nystatin can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein is a method of treating or preventing an infection, the method comprising: (i) mixing a compounded composition comprising mupirocin and nystatin with a diluent to create a solution; (ii) adding the solution to water contained within a foot bath; (iii) agitating the water contained within the foot bath; and (iv) contacting the agitated water with at least part of one or both feet of a subject.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the compounded composition and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the compounded composition can comprise an excipient base powder comprising a blend of micronized xylitol and poloxamers.

In an aspect, the compounded composition can be a dry powder formulation.

In an aspect, the mupirocin can be a dry powder. In an aspect, the mupirocin can be an ointment. In an aspect, the mupirocin can be a 2% ointment. The mupirocin can be pure or substantially pure. The mupirocin can be obtained from a bulk source. In an aspect, the nystatin can be a dry powder. In an aspect, the nystatin can be an ointment. The nystatin can be pure or substantially pure. The nystatin can be obtained from a bulk source.

In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can comprise from about 10% to about 40% w/w of the compounded composition. In an aspect, the mupirocin can comprise from about 15% to about 35% w/w of the compounded composition. In an aspect, the mupirocin can comprise from about 20% to about 30% w/w of the compounded composition. In an aspect, the mupirocin can comprise about 25% w/w of the compounded composition.

In an aspect, the nystatin can comprise from about 10% to about 40% w/w of the compounded composition. In an aspect, the nystatin can comprise from about 15% to about 35% w/w of the compounded composition. In an aspect, the nystatin can comprise from about 20% to about 30% w/w of the compounded composition. In an aspect, the nystatin can comprise about 25% w/w of the compounded composition.

In an aspect, the ratio of the mupirocin to the nystatin in the compounded composition can be from about 1:4 to about 4:1. In an aspect, the ratio of the mupirocin to the nystatin can be about 1:1. In an aspect, the ratio of the mupirocin to the nystatin can be about 1.25:1. See, e.g., Table 3.

In an aspect, a disclosed compounded composition can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, a disclosed compounded composition comprising mupirocin and nystatin can be encapsulated in one or more capsules. In an aspect, the one or more capsules comprising the compounded composition can be added to the water contained within the foot bath. In an aspect, the one or more capsules can disintegrate and the compounded composition can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

C. Methods of Treating of Preventing an Infection Using Anti-Infective Agents

Disclosed herein is a method of treating or preventing an infection, the method comprising: (i) adding one or more powders to water contained within a foot bath; (ii) agitating the water contained within the foot bath; and (iii) contacting the agitated water with at least a part of one or both feet of a subject.

1. Anti-Bacterial Agent and/or Anti-Fungal Agent

Disclosed herein is a method of treating or preventing an infection, the method comprising: (i) adding an anti-bacterial agent to water contained within a foot bath; (ii) adding an anti-fungal agent to the water, (iii) agitating the water contained within the foot bath; and (iv) contacting the agitated water with at least a part of one or both feet of a subject.

In an aspect, the anti-bacterial agent be a dry powder. In an aspect, the anti-bacterial agent can be an ointment. In an aspect, the anti-bacterial agent can be obtained from a bulk source. The anti-bacterial agent can be pure or substantially pure.

In an aspect, the anti-fungal agent be a dry powder. In an aspect, the anti-fungal agent can be an ointment. In an aspect, the anti-fungal agent can be obtained from a bulk source. The anti-fungal agent can be pure or substantially pure.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed method, the anti-bacterial agent can comprise mupirocin.

In an aspect of a disclosed method, the anti-bacterial agent can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed method, the anti-fungal agent can comprise fluconazole. In an aspect of a disclosed method, the anti-fungal agent can comprise itraconazole. In an aspect of a disclosed method, the anti-fungal agent can comprise nystatin.

In an aspect of a disclosed method, the anti-bacterial agent can comprise mupirocin and the anti-fungal agent can comprise itraconazole. In an aspect of a disclosed method, the anti-bacterial agent can comprise azithromycin and the anti-fungal agent can comprise fluconazole. In an aspect of a disclosed method, the anti-bacterial agent can comprise mupirocin and the anti-fungal agent can comprise nystatin.

In an aspect, the amount of the anti-bacterial agent added to the water compared to the amount of the anti-fungal agent added to the water can be from about 1:4 to about 4:1. In an aspect, the ratio can be about 1:1. In an aspect, the ratio of the anti-bacterial agent to the anti-fungal agent be about 1.25:1. See, e.g., Table 1.

In an aspect, the amount of the anti-bacterial agent can be from about 125 mg to about 2000 mg. In an aspect, the amount of the anti-fungal agent can be from about 125 mg to about 2000 mg.

In an aspect of a disclosed method, the amount of the anti-bacterial agent can be about 250 mg and the amount of the anti-fungal agent can be about 250 mg. In an aspect of a disclosed method, the amount of the anti-bacterial agent ca be about 250 mg and the amount of the anti-fungal agent can be about 500 mg. In an aspect of a disclosed method, the amount of the anti-bacterial agent can be about 500 mg and the amount of the anti-fungal agent can be about 500 mg. In an aspect of a disclosed method, the amount of the anti-bacterial agent can be about 1000 mg and the amount of the anti-fungal agent can be about 500 mg.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the anti-bacterial agent or the anti-fungal agent or both throughout the water contained within the foot bath. Heating agents and/or means to heat water in a compartment are known to the art.

In an aspect, the method can comprise adding to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the method can comprise adding to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed anti-bacterial agent can be encapsulated in one or more capsules. In an aspect, the one or more capsules comprising the anti-bacterial agent can be added to the water contained within the foot bath. In an aspect, the one or more capsules can disintegrate and the anti-bacterial agent can be dissolved in the water contained within the foot bath. In an aspect, a subject can open or break apart the one or more capsule and pour the contents of the opened or broken capsules into the water contained within a foot bath.

In an aspect, a disclosed an anti-fungal agent can be encapsulated in one or more capsules. In an aspect, the one or more capsules comprising the anti-fungal agent can be added to the water contained within the foot bath. In an aspect, the one or more capsules can disintegrate and the anti-fungal can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein a method of treating or preventing an infection, the method comprising: (i) mixing an anti-bacterial agent, an anti-fungal agent, and a diluent to form a solution; (ii) adding the solution to water contained within a foot bath; (iii) agitating the water contained within the foot bath; and (iv) contacting the agitated water with at least part of one or both feet of a subject.

In an aspect, the anti-bacterial agent, the anti-fungal agent, and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the anti-bacterial agent be a dry powder. In an aspect, the anti-bacterial agent can be an ointment. In an aspect, the anti-bacterial agent can be obtained from a bulk source. The anti-bacterial agent can be pure or substantially pure.

In an aspect, the anti-fungal agent be a dry powder. In an aspect, the anti-fungal agent can be an ointment. In an aspect, the anti-fungal agent can be obtained from a bulk source. The anti-fungal agent can be pure or substantially pure.

In an aspect, the anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof.

In an aspect of a disclosed method, the anti-bacterial agent can comprise mupirocin. In an aspect of a disclosed method, the anti-bacterial agent can comprise azithromycin.

In an aspect, the anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof.

In an aspect of a disclosed method, the anti-fungal agent can comprise fluconazole. In an aspect of a disclosed method, the anti-fungal agent can comprise itraconazole. In an aspect of a disclosed method, the anti-fungal agent can comprise nystatin.

In an aspect of a disclosed method, the anti-bacterial agent can comprise mupirocin and the anti-fungal agent can comprise itraconazole. In an aspect of a disclosed method, the anti-bacterial agent can comprise azithromycin and the anti-fungal agent can comprise fluconazole. In an aspect of a disclosed method, the anti-bacterial agent can comprise mupirocin and the anti-fungal agent can comprise nystatin.

In an aspect, the amount of the anti-bacterial agent added to the diluent compared to the amount of the anti-fungal agent added to the diluent can be from about 1:4 to about 4:1. In an aspect, the ratio can be about 1:1. In an aspect, the ratio of the anti-bacterial agent to the anti-fungal agent be about 1.25:1. See, e.g., Table 1.

In an aspect, the amount of the anti-bacterial agent can be from about 125 mg to about 2000 mg. In an aspect, the amount of the anti-fungal agent can be from about 125 mg to about 2000 mg. In an aspect of a disclosed method, the amount of the anti-bacterial agent can be about 250 mg and the amount of the anti-fungal agent can be about 250 mg. In an aspect of a disclosed method, the amount of the anti-bacterial agent ca be about 250 mg and the amount of the anti-fungal agent can be about 500 mg. In an aspect of a disclosed method, the amount of the anti-bacterial agent can be about 500 mg and the amount of the anti-fungal agent can be about 500 mg. In an aspect of a disclosed method, the amount of the anti-bacterial agent can be about 1000 mg and the amount of the anti-fungal agent can be about 500 mg.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the method can comprise adding to the diluent or to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the method can comprise adding to the diluent or to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, a disclosed anti-bacterial agent can be encapsulated in one or more capsules. In an aspect, the one or more capsules comprising the anti-bacterial agent can be added to the diluent. In an aspect, the one or more capsules can diluent. In an aspect, a subject can open or break apart the one or more capsule and pour the contents of the opened or broken capsules into the diluent.

In an aspect, a disclosed an anti-fungal agent can be encapsulated in one or more capsules. In an aspect, the one or more capsules comprising the anti-fungal agent can be added to the diluent. In an aspect, the one or more capsules can disintegrate and the anti-fungal can be dissolved in the diluent. In an aspect, a subject can open or break apart the one or more capsule and pour the contents of the opened or broken capsules into the diluent.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

2. Mupirocin and/or Itraconazole Powders

Disclosed herein is a method of treating or preventing an infection, the method comprising: (i) adding mupirocin to water contained within a foot bath; (ii) adding an itraconazole to the water, (iii) agitating the water contained within the foot bath; and (iv) contacting the agitated water with at least a part of one or both feet of a subject.

In an aspect, the mupirocin be a dry powder. In an aspect, the mupirocin can be an ointment. In an aspect, the mupirocin can be obtained from a bulk source. The mupirocin can be pure or substantially pure. In an aspect, the itraconazole be a dry powder. In an aspect, the itraconazole can be an ointment. In an aspect, the itraconazole can be obtained from a bulk source. The itraconazole can be pure or substantially pure.

In an aspect, the amount of the mupirocin added to the water compared to the amount of the itraconazole added to the water can be from about 1:4 to about 4:1. In an aspect, the ratio of the mupirocin to the itraconazole can be about 1:1. In an aspect, the ratio of the mupirocin to the itraconazole can be about 1.25:1. See, e.g., Table 1.

In an aspect, the amount of the mupirocin can be from about 125 mg to about 2000 mg. In an aspect, the amount of the itraconazole can be from about 125 mg to about 2000 mg. In an aspect, the amount of the mupirocin can be about 500 mg and the amount of the itraconazole can be about 500 mg. In an aspect, the amount of the mupirocin can be about 1000 mg and the amount of the itraconazole can be about 500 mg.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the mupirocin or the itraconazole or both throughout the water contained within the foot bath. Heating agents and/or means to heat water in a compartment are known to the art.

In an aspect, the method can comprise adding to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise adding to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the mupirocin can be encapsulated in one or more capsules. In an aspect, the one or more capsules comprising the mupirocin can be added to the water contained within the foot bath. In an aspect, the one or more capsules can disintegrate and the mupirocin can be dissolved in the water contained within the foot bath. In an aspect, a subject can open or break apart the one or more capsule and pour the contents of the opened or broken capsules into the water contained within a foot bath.

In an aspect, the itraconazole can be encapsulated in one or more capsules. In an aspect, the one or more capsules comprising the itraconazole can be added to the water contained within the foot bath. In an aspect, the one or more capsules can disintegrate and the itraconazole can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein a method of treating or preventing an infection, the method comprising: (i) mixing mupirocin, itraconazole, and a diluent to form a solution; (ii) adding the solution to water contained within a foot bath; (iii) agitating the water contained within the foot bath; and (iv) contacting the agitated water with at least part of one or both feet of a subject.

In an aspect, the mupirocin can be a dry powder. In an aspect, the mupirocin can be an ointment. In an aspect, the mupirocin can be obtained from a bulk source. The mupirocin can be pure or substantially pure.

In an aspect, the itraconazole can be a dry powder. In an aspect, the itraconazole can be an ointment. In an aspect, the itraconazole can be obtained from a bulk source. The itraconazole can be pure or substantially pure.

In an aspect, the amount of the mupirocin used compared to the amount of the itraconazole used can be from about 1:4 to about 4:1. In an aspect, the ratio can be about 1:1. In an aspect, the ratio of the mupirocin to the itraconazole can be about 1.25:1. See, e.g., Table 1.

In an aspect, the amount of the mupirocin can be from about 125 mg to about 2000 mg. In an aspect, the amount of the itraconazole can be from about 125 mg to about 2000 mg.

In an aspect, the amount of the mupirocin can be about 500 mg and the amount of the itraconazole can be about 500 mg. In an aspect, the amount of the mupirocin can be about 1000 mg and the amount of the itraconazole can be about 1000 mg. In an aspect, the amount of the mupirocin can be about 1000 mg and the amount of the itraconazole can be about 500 mg.

In an aspect, the mupirocin, the itraconazole, and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the method can comprise adding to the solution or to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise adding to the solution or to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the mupirocin can be encapsulated in one or more capsules. In an aspect, the one or more capsules comprising the mupirocin can be added to the diluent. In an aspect, the one or more capsules can disintegrate and the mupirocin can be dissolved in the diluent. In an aspect, a subject can open or break apart the one or more capsule and pour the contents of the opened or broken capsules into the diluent.

In an aspect, the itraconazole can be encapsulated in one or more capsules. In an aspect, the one or more capsules comprising the itraconazole can be added to the diluent. In an aspect, the one or more capsules can disintegrate and the itraconazole can be dissolved in the diluent. In an aspect, a subject can open or break apart the one or more capsule and pour the contents of the opened or broken capsules into the diluent.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

3. Azithromycin and/or Fluconazole Powders

Disclosed herein is a method of treating or preventing an infection, the method comprising: (i) adding azithromycin to water contained within a foot bath; (ii) adding fluconazole to the water, (iii) agitating the water contained within the foot bath; and (iv) contacting the agitated water with at least a part of one or both feet of a subject.

In an aspect, the azithromycin be a dry powder. In an aspect, the azithromycin can be an ointment. In an aspect, the azithromycin can be obtained from a bulk source. The azithromycin can be pure or substantially pure.

In an aspect, the fluconazole be a dry powder. In an aspect, the fluconazole can be an ointment. In an aspect, the fluconazole can be obtained from a bulk source. The fluconazole can be pure or substantially pure. In an aspect, the amount of the azithromycin added to the water compared to the amount of the fluconazole added to the water can be from about 1:4 to about 4:1. In an aspect, the ratio can be about 1:1. In an aspect, the ratio of the azithromycin to the fluconazole can be about 1.25:1.

In an aspect of a disclosed method, the amount of the azithromycin can be about 250 mg and the amount of the fluconazole can be about 250 mg. In an aspect of a disclosed method, the amount of the azithromycin can be about 250 mg and the amount of the fluconazole can be about 500 mg. In an aspect of a disclosed method, the amount of the azithromycin can be about 500 mg and the amount of the fluconazole can be about 500 mg. In an aspect of a disclosed method, the amount of the azithromycin can be about 1000 mg and the amount of the fluconazole can be about 500 mg.

In an aspect, the method can comprise adding a diluent to the water contained in the foot bath. In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the azithromycin or the fluconazole or both throughout the water contained within the foot bath. Heating agents and/or means to heat water in a compartment are known to the art.

In an aspect, the method can comprise adding to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the method can comprise adding to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the azithromycin can be encapsulated in one or more capsules. In an aspect, the one or more capsules comprising the azithromycin can be added to the water contained within the foot bath. In an aspect, the one or more capsules can disintegrate and the azithromycin can be dissolved in the water contained within the foot bath. In an aspect, a subject can open or break apart the one or more capsule and pour the contents of the opened or broken capsules into the water contained within a foot bath.

In an aspect, the fluconazole can be encapsulated in one or more capsules. In an aspect, the one or more capsules comprising the a fluconazole can be added to the water contained within the foot bath. In an aspect, the one or more capsules can disintegrate and the fluconazole can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein a method of treating or preventing an infection, the method comprising: (i) mixing azithromycin, fluconazole, and a diluent to form a solution; (ii) adding the solution to water contained within a foot bath; (iii) agitating the water contained within the foot bath; and (iv) contacting the agitated water with at least part of one or both feet of a subject.

In an aspect, the azithromycin be a dry powder. In an aspect, the azithromycin can be an ointment. In an aspect, the azithromycin can be obtained from a bulk source. The azithromycin can be pure or substantially pure. In an aspect, the fluconazole be a dry powder. In an aspect, the fluconazole can be an ointment. In an aspect, the fluconazole can be obtained from a bulk source. The fluconazole can be pure or substantially pure.

In an aspect, the amount of the azithromycin used compared to the amount of the fluconazole used can be from about 1:4 to about 4:1. In an aspect, the ratio can be about 1:1. In an aspect, the ratio of the azithromycin to the fluconazole can be about 1.25:1.

In an aspect, the amount of the azithromycin can be from about 125 mg to about 2000 mg. In an aspect, the amount of the fluconazole can be from about 125 mg to about 2000 mg.

In an aspect of a disclosed method, the amount of the azithromycin can be about 250 mg and the amount of the fluconazole can be about 250 mg. In an aspect of a disclosed method, the amount of the azithromycin can be about 250 mg and the amount of the fluconazole can be about 500 mg. In an aspect of a disclosed method, the amount of the azithromycin can be about 500 mg and the amount of the fluconazole can be about 500 mg. In an aspect of a disclosed method, the amount of the azithromycin can be about 1000 mg and the amount of the fluconazole can be about 500 mg.

In an aspect, the azithromycin, the fluconazole, and the diluent can be mixed in a mixing container. In an aspect, a mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the diluent can comprise sodium hypochlorite. In an aspect, the diluent can comprise Dakin's solution. In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution the water contained within the foot bath. Heating agents and/or means to heat water in a compartment are known to the art.

In an aspect, the method can comprise adding to the diluent or to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the method can comprise adding to the diluent or to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the azithromycin can be encapsulated in one or more capsules. In an aspect, the one or more capsules comprising the azithromycin can be added to the water contained within the foot bath. In an aspect, the one or more capsules can disintegrate and the azithromycin can be dissolved in the water contained within the foot bath. In an aspect, a subject can open or break apart the one or more capsule and pour the contents of the opened or broken capsules into the water contained within a foot bath.

In an aspect, the fluconazole can be encapsulated in one or more capsules. In an aspect, the one or more capsules comprising the a fluconazole can be added to the water contained within the foot bath. In an aspect, the one or more capsules can disintegrate and the fluconazole can be dissolved in the water contained within the foot bath. In an aspect, a subject can open or break apart the one or more capsule and pour the contents of the opened or broken capsules into the water contained within a foot bath.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

4. Mupirocin and/or Nystatin

Disclosed herein is a method of treating or preventing an infection, the method comprising: (i) adding mupirocin to water contained in a foot bath, (ii) adding nystatin to the water, (iii) agitating the water contained within the foot bath; and (iv) contacting the agitated water with at least a part of one or both feet of a subject.

In an aspect, the mupirocin can be a dry powder. In an aspect, the mupirocin can be obtained from a bulk source. The mupirocin can be pure or substantially pure. In an aspect, the mupirocin can be an ointment. In an aspect, the mupirocin can be a 2% ointment. In an aspect, the mupirocin can be provided in a tube. For example, in an aspect, the mupirocin can be provided in a 22 gram tube. In an aspect, the nystatin can be a dry powder. In an aspect, the nystatin can be an ointment. In an aspect, the nystatin can be obtained from a bulk source. The nystatin can be pure or substantially pure. In an aspect, the nystatin can be provided in a container. For example, in an aspect, the nystatin can be provided in 15 gram container.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(iv) daily. In an aspect, the method can comprise repeating steps (i)-(iv) daily until the bacterial infection or suspected bacterial infection can be eradicated. In an aspect, the method can comprise repeating steps (i)-(iv) daily until the fungal infection or suspected fungal infection can be eradicated. In an aspect, the method can comprise repeating steps (i)-(iv) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the mupirocin and the nystatin or both throughout the water contained within the foot bath. Heating agents and/or means to heat water in a compartment are known to the art.

In an aspect, the method can comprise adding to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the method can comprise adding a 22 gram tube of mupirocin to the water and adding a 15 gram container of nystatin to the water.

In an aspect, the method can comprise adding to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

Disclosed herein is a method of treating or preventing an infection, the method comprising: (i) adding mupirocin to a mixing container, (ii) adding nystatin to the mixing container, (iii) adding a diluent to the mixing container, (iv) mixing the mupirocin, nystatin, and diluent in the mixing container to form a solution, (v) adding the solution to water contained within a foot bath; (vi) agitating the water contained within the foot bath; and (vii) contacting the agitated water with at least a part of one or both feet of a subject.

In an aspect, the mixing container can have a pre-determined size that can measure or hold a pre-determined amount or volume. For example, in an aspect, a mixing container can measure or hold an amount of about 1 ounces to about 30 ounces. In an aspect, the mixing container can hold about 6 ounces. In an aspect, the mixing container can hold about 16 ounces.

In an aspect, the diluent can comprise sodium hypochlorite. In an aspect, the diluent can comprise Dakin's solution.

In an aspect, the amount of diluent can be about 3.75 mL to about 60 mL. In an aspect, the amount of diluent can be about 15 mL.

In an aspect, the subject has been diagnosed with or is suspected of having a bacterial infection that affects at least part of one or both feet. In an aspect, the subject has been diagnosed with or is suspected of having a fungal infection that affects at least part of one or both feet. In an aspect, the subject has been diagnosed with or is suspected of having a bacterial infection and a fungal infection that affect at least part of one or both feet.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise repeating steps (i)-(vii) daily. In an aspect, the method can comprise repeating steps (i)-(vii) daily until the bacterial infection or suspected bacterial infection can be eradicated. In an aspect, the method can comprise repeating steps (i)-(vii) daily until the fungal infection or suspected fungal infection can be eradicated. In an aspect, the method can comprise repeating steps (i)-(vii) daily until the infection or the suspected infection can be eradicated.

In an aspect, the method can comprise heating the water contained within the foot bath.

In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the solution throughout the water contained within the foot bath. Heating agents and/or means to heat water in a compartment are known to the art.

In an aspect, the method can comprise adding to the diluent or to the water an excipient base powder comprising a blend of micronized xylitol and poloxamers. In an aspect, the excipient base powder can comprise Loxasperse™ excipient base powder. In an aspect, the excipient base powder can comprise Loxasperse™ excipient base powder and XyliFos™ excipient base powder. In an aspect, an excipient base powder can be obtained from a bulk source.

In an aspect, the mupirocin can be a dry powder. In an aspect, the mupirocin can be obtained from a bulk source. The mupirocin can be pure or substantially pure. In an aspect, the mupirocin can be an ointment. In an aspect, the mupirocin can be a 2% ointment. In an aspect, the mupirocin can be provided in a tube. For example, in an aspect, the mupirocin can be provided in a 22 gram tube. In an aspect, the nystatin can be a dry powder. In an aspect, the nystatin can be an ointment. In an aspect, the nystatin can be obtained from a bulk source. The nystatin can be pure or substantially pure. In an aspect, the nystatin can be provided in a container. For example, in an aspect, the nystatin can be provided in 15 gram container.

In an aspect, the method can comprise adding a 22 gram tube of mupirocin to the mixing container and adding a 15 gram container of nystatin to the mixing container.

In an aspect, adding the mupirocin to the mixing container can comprise attaching a key (e.g., a metal key) to an end of a tube of mupirocin and sliding the key down the length of the tube towards the aperture of the tube, thereby forcing the contents of the tube into the mixing container.

In an aspect, the method can comprise adding to the mixing container or to the water one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an anti-bacterial agent. Anti-bacterial agents are known to the art and discussed supra. In an aspect, the additional anti-infective agent can be an anti-fungal agent. Anti-fungal agents are known to the art and discussed supra.

In an aspect, the method can comprise orally administering to the subject a pharmaceutical composition comprising an anti-bacterial agent. Anti-bacterial agents are known to the art and discussed supra. In an aspect, the method can comprise orally administering to the subject a pharmaceutical composition comprising an anti-fungal agent. Anti-fungal agents are known to the art and discussed supra. In an aspect, the method can comprise orally administering to the subject a pharmaceutical composition comprising an anti-bacterial agent and a pharmaceutical composition comprising an anti-fungal agent.

In an aspect, the mupirocin can be encapsulated in one or more capsules. In an aspect, the one or more capsules comprising the mupirocin can be added to the diluent. In an aspect, the one or more capsules can disintegrate and the mupirocin can be dissolved in the diluent. In an aspect, a subject can open or break apart the one or more capsule and pour the contents of the opened or broken capsules into the diluent.

In an aspect, the nystatin can be encapsulated in one or more capsules. In an aspect, the one or more capsules comprising the nystatin can be added to the diluent. In an aspect, the one or more capsules can disintegrate and the nystatin can be dissolved in the diluent. In an aspect, a subject can open or break apart the one or more capsule and pour the contents of the opened or broken capsules into the diluent.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

D. Expected Efficacy of Various Anti-Infective Agents

Table 4 shows the expected efficacy of anti-fungal agents against various fungi.

Tables 5 and 6 show the expected efficacy of anti-bacterial agents against various bacteria.

TABLE 4

EFFICACY OF VARIOUS ANTIFUNGAL AGENTS

| | Fluconazole | Itraconazole | Voriconazole | Amphotericin | Nystatin |
|---|---|---|---|---|---|
| *Aspergillus flavus* | yes | yes | yes | yes | |
| *Aspergillus fumigatus* | yes | yes | yes | yes | |
| *Aspergillus niger* | | | yes | yes | |
| *Aspergillus terreus* | | | yes | yes | |
| *Blastomyces dermatitidis* | yes | yes | | yes | |
| *Candida* species | yes | yes | yes | yes | yes |
| *Coccidioides immitis* | yes | yes | | yes | |
| *Cryptococcus neoformans* | yes | yes | | yes | |
| *Fusarium* species | | | yes | | |
| *Histoplasma capsulatum* | yes | | | yes | |
| *Histoplasma duboisii* | | yes | | | |
| *Leishmania donovani* | | | | yes | |
| *Leishmania infantum* | | | | yes | |
| *Paracoccidioides brasiliensis* | | yes | | yes | |
| *Scedosporium apiospermum* | | | yes | | |
| *Sporothrix schenckii* | | yes | | | |
| *Trichophyton mentagrophytes* | | yes | | | |
| *Trichophyton rubrum* | | yes | | | |

TABLE 5

EFFICACY OF VARIOUS ANTIBIOTIC AGENTS

| | Gram | Bactroban | Ceftriaxone | Vancomycin | Colistimethate | Ciprofloxacin |
|---|---|---|---|---|---|---|
| *Bacteroides fragilis* | anaer | | yes | no | no | no |
| *Clostridium difficile* | anaer | | no | yes | no | no |
| *Clostridium perfringens* | anaer | no | yes | no | | |
| *Chlamydia pneumoniae* | n/a | | no | no | no | yes |
| *Chlamydia psittaci* | n/a | | no | no | no | |
| *Chlamydia trachomatis* | n/a | | no | no | no | |
| *Mycoplasma pneumoniae* | n/a | | no | no | no | yes |
| *Acinetobacter baumannii* | neg | no | no | no | ± | ± |
| *Acinetobacter calcoaceticus* | neg | no | no | no | ± | ± |
| *Acinetobacter lwoffii* | neg | no | no | no | ± | ± |
| *Bartonella bacilliformis* | neg | no | ± | no | | yes |
| *Bordetella pertussis* | neg | no | no | no | no | ± |
| *Brucella* species | neg | no | ± | no | no | ± |
| *Campylobacter jejuni* | neg | no | no | no | | yes |
| *Citrobacter diversus* | neg | no | yes | no | | yes |
| *Citrobacter freundii* | neg | no | yes | no | | yes |
| *Enterobacter aerogenes* | neg | no | yes | no | yes | yes |
| *Enterobacter cloacae* | neg | no | yes | no | yes | yes |
| *Enterobacter sakazakii* | neg | no | yes | no | yes | |
| *Escherichia coli* | neg | no | yes | no | yes | yes |
| *Francisella tularensis* | neg | no | no | no | | yes |
| *Haemophilus ducreyi* | neg | no | yes | no | | |
| *Haemophilus influenzae* | neg | no | yes | no | | yes |
| *Haemophilus parainfluenzae* | neg | | yes | no | no | yes |
| *Klebsiella (Calymmatobacterium) granulomatis* | neg | no | yes | no | yes | |
| *Klebsiella oxytoca* | neg | no | yes | no | yes | yes |
| *Klebsiella pneumoniae* | neg | no | yes | no | yes | yes |
| *Legionella pneumophila* | neg | no | no | no | no | yes |
| *Moraxella catarrhalis* | neg | no | yes | no | no | yes |
| *Morganella morganii* | neg | no | yes | no | | yes |
| *Neisseria gonorrhoeae* | neg | no | yes | no | no | yes |
| *Neisseria meningitidis* | neg | no | yes | no | no | yes |
| *Proteus mirabilis* | neg | no | yes | no | no | yes |
| *Proteus vulgaris* | neg | no | yes | no | no | yes |
| *Providencia rettgeri* | neg | no | yes | no | no | yes |
| *Providencia stuartii* | neg | no | yes | no | no | yes |
| *Pseudomonas aeruginosa* | neg | no | no | no | yes | yes |
| *Pseudomonas fluorescens* | neg | no | ± | no | yes | yes |
| *Rickettsiae* | neg | no | no | no | | yes |
| *Salmonella typhi* | neg | no | yes | no | | yes |
| *Serratia marcescens* | neg | no | yes | no | no | yes |
| *Shigella boydii* | neg | no | yes | no | | yes |
| *Shigella dysenteriae* | neg | no | yes | no | | yes |
| *Shigella flexneri* | neg | no | yes | no | | yes |
| *Shigella sonnei* | neg | no | yes | no | | yes |
| *Vibrio cholerae* | neg | no | no | no | no | yes |
| *Yersinia pestis* | neg | no | no | no | | yes |
| *Corynebacterium jeikeium* | pos | no | no | yes | no | no |
| *Corynebacterium urealyticum* | pos | no | no | yes | no | ± |
| Diphtheroids | pos | no | no | yes | no | |
| *Enterococcus faecalis* | pos | no | no | yes | no | ± |

TABLE 5-continued

EFFICACY OF VARIOUS ANTIBIOTIC AGENTS

|  | Gram | Bactroban | Ceftriaxone | Vancomycin | Colistimethate | Ciprofloxacin |
|---|---|---|---|---|---|---|
| *Enterococcus faecium* | pos |  | no | yes, not VRE | no | no |
| Methicillin resistant *staph aureus* (MRSA) | pos | yes | no | yes | no | no |
| *Peptostreptococcus* | pos |  | yes | yes | no | ± |
| *Staphylococcus aureus* (MSSA) | pos | yes | yes | yes | no | ± |
| *Staphylococcus epidermidis* | pos |  | yes | yes | no | yes |
| *Streptococcus agalactiae* | pos |  | yes | yes | no | ± |
| *Streptococcus pneumoniae* | pos |  | yes | yes | no | ± |
| *Streptococcus pyogenes* | pos | yes | yes | yes | no | ± |
| Viridans group streptococci | pos |  | yes | yes | no | ± |

TABLE 6

EFFICACY OF VARIOUS ANTIBIOTIC AGENTS

|  | Levofloxacin | Tobramycin | Doxycycline | Azithromycin | Clindamycin | Sulfa/Trim |
|---|---|---|---|---|---|---|
| *Bacteroides fragilis* | no | no | ± | no | yes | no |
| *Clostridium difficile* | no | no | ± | no | ± | no |
| *Clostridium perfringens* | yes | no |  | no | yes - partial | no |
| *Chlamydia pneumoniae* | yes | no | yes | yes | ± | no |
| *Chlamydia psittaci* |  | no | yes | yes | no | no |
| *Chlamydia trachomatis* |  | no | yes | yes | no | no |
| *Mycoplasma pneumoniae* | yes | no | ± | yes | no | no |
| *Acinetobacter baumannii* | ± | no | no | no | no | ± |
| *Acinetobacter calcoaceticus* | ± | no | ± | no | no | ± |
| *Acinetobacter lwoffii* | ± | no | no | no | no | ± |
| *Bartonella bacilliformis* | yes | ± | yes | yes | no | yes |
| *Bordetella pertussis* | ± | no |  | yes | no | yes |
| *Brucella* species | ± | ± | yes | no | no | yes |
| *Campylobacter jejuni* | yes | yes | yes | yes | no | no |
| *Citrobacter diversus* | yes | yes | no | no | no | no |
| *Citrobacter freundii* | yes | yes | no | no | no | no |
| *Enterobacter aerogenes* | yes | yes | ± | no | no | yes |
| *Enterobacter cloacae* | yes | yes | ± | no | no | yes |
| *Enterobacter sakazakii* | yes | yes | ± | no | no | no |
| *Escherichia coli* | yes | yes | ± | no | no | yes |
| *Francisella tularensis* | yes | ± | yes | no | no | no |
| *Haemophilus ducreyi* |  | yes | yes |  |  | ± |
| *Haemophilus influenzae* | yes | yes | yes | yes | no | ± |
| *Haemophilus parainfluenzae* | yes |  | yes |  | no | no |
| *Klebsiella* (*Calymmatobacterium*) |  | yes | yes | no | no | yes |
| *Klebsiella oxytoca* | yes | yes | ± | no | no | yes |
| *Klebsiella pneumoniae* | yes | yes | ± | no | no | yes |
| *Legionella pneumophila* | yes | no | yes | yes | no | no |
| *Moraxella catarrhalis* | yes | yes | yes | yes | no | yes |
| *Morganella morganii* | yes | ± | no | no | no | yes |
| *Neisseria gonorrhoeae* | yes | no | ± | ± | no | ± |
| *Neisseria meningitidis* | yes | no | yes | yes | no | yes |
| *Proteus mirabilis* | yes | yes | no | no | no | no |
| *Proteus vulgaris* | yes | yes | no | no | no | no |
| *Providencia rettgeri* | yes | ± | no | no | no | ± |
| *Providencia stuartii* | yes | ± | no | no | no | ± |
| *Pseudomonas aeruginosa* | yes | yes | no | no | no | no |
| *Pseudomonas fluorescens* | yes | yes |  | no | no | ± |
| *Rickettsiae* | yes |  | yes | yes | no | no |
| *Salmonella typhi* | yes |  | ± | ± | no | ± |
| *Serratia marcescens* | yes | yes | no | no | no | ± |
| *Shigella boydii* | yes | yes | ± | ± | no | ± |
| *Shigella dysenteriae* | yes | yes | ± | ± | no | ± |
| *Shigella flexneri* | yes | yes | ± | ± | no | ± |
| *Shigella sonnei* | yes | yes | ± | ± | no | ± |
| *Vibrio cholerae* | yes | no | yes | yes | no | yes |
| *Yersinia pestis* | yes | yes | yes | ± | no | yes |
| *Corynebacterium jeikeium* | no | no |  | no |  |  |
| *Corynebacterium urealyticum* | ± | no | ± | ± |  | no |
| Diphtheroids |  | no |  |  |  |  |
| *Enterococcus faecalis* | yes | no | no | no | no | no |
| *Enterococcus faecium* | no | no | no | no | no | ± |
| Methicillin resistant *staph* | no | no | ± | no | no | yes |

TABLE 6-continued

EFFICACY OF VARIOUS ANTIBIOTIC AGENTS

|  | Levofloxacin | Tobramycin | Doxycycline | Azithromycin | Clindamycin | Sulfa/Trim |
|---|---|---|---|---|---|---|
| *aureus* (MRSA) | | | | | | |
| *Peptostreptococcus* | ± | no | ± | ± | yes | yes |
| *Staphylococcus aureus* (MSSA) | yes | no | ± | yes | yes | yes |
| *Staphylococcus epidermidis* | yes | no | yes | yes | yes | yes |
| *Streptococcus agalactiae* | yes | no | ± | yes | yes | yes |
| *Streptococcus pneumoniae* | yes | no | yes | yes | yes | yes |
| *Streptococcus pyogenes* | yes | no | ± | yes | yes | ± |
| Viridans group streptococci | yes | no | ± | ± | yes | yes |

What is claimed is:

1. A method for treating a fungal or bacterial infection of a subject's foot, the method comprising:
   (i) mixing mupirocin, itraconazole, and a diluent to form a solution;
   (ii) adding the solution to water contained within a foot bath;
   (iii) agitating the water contained within the foot bath; and
   (iv) contacting the agitated water with at least part of one or both feet of the subject.

2. The method of claim 1, wherein the amount of mupirocin comprises about 500 mg and wherein the amount of the itraconazole comprises about 500 mg.

3. The method of claim 1, wherein the ratio of mupirocin to itraconazole comprises about 1:1.

4. The method of claim 1, wherein the diluent comprises sodium hypochlorite or a solution of sodium hypochlorite.

5. The method of claim 1, wherein the subject has been diagnosed with or is suspected of having an infection that affects at least part of one or both feet.

6. The method of claim 1, wherein contacting comprises placing at least part of one or both feet of the subject in the foot bath for about 10 minutes.

7. The method of claim 1, comprising repeating steps (i)-(iv) daily.

8. The method of claim 1, comprise adding to the solution or to the water an excipient base powder.

9. The method of claim 8, wherein the excipient base powder comprises an excipient base powder comprising micronized xylitol and micronized poloxamers or the excipient base powder comprises an excipient base powder comprising micronized xylitol and micronized poloxamers and an excipient base powder comprising xylitol, poloxamer 407, hydroxylpropyl betadex, and epigallocatechin gallate.

10. The method of claim 1, comprising orally administering to the subject a pharmaceutical composition comprising an anti-bacterial agent, a pharmaceutical composition comprising an anti-fungal agent, or both.

\* \* \* \* \*